United States Patent
Christensen et al.

(10) Patent No.: US 9,253,952 B2
(45) Date of Patent: Feb. 9, 2016

(54) AGROBACTERIUM RHIZOGENES TRANSFORMATION AND EXPRESSION OF ROL GENES IN KALANCHOË

(75) Inventors: Ellen Margrethe Skovsgaard Christensen, Hinnerup (DK); Renate Petra Brigitte Müller, Malmö (SE); Henrik Vlk Lütken, Broenshoj (DK); Josefine Nymark Hegelund, Skibby (DK); Line Jensen, Lundby (DK); Brian Christensen, København (DK); Else Bollerup Jensen, Skanderborg (DK); Kai Lønne Nielsen, Hinnerup (DK)

(73) Assignees: UNIVERSITY OF COPENHAGEN, Copenhagen (DK); KNUD JEPSEN A/S, Hinnerup (DK)

( * ) Notice: Subject to any disclaimer, the term of this patent is extended or adjusted under 35 U.S.C. 154(b) by 451 days.

(21) Appl. No.: 13/588,668

(22) Filed: Aug. 17, 2012

(65) Prior Publication Data

US 2014/0053297 A1   Feb. 20, 2014

(51) Int. Cl.
*C12N 15/82* (2006.01)
*A01H 4/00* (2006.01)
*A01H 3/00* (2006.01)
*A01H 5/02* (2006.01)

(52) U.S. Cl.
CPC .............. *A01H 3/00* (2013.01); *A01H 5/0266* (2013.01); *C12N 15/8205* (2013.01); *C12N 15/8261* (2013.01)

(58) Field of Classification Search
None
See application file for complete search history.

(56) References Cited

U.S. PATENT DOCUMENTS

| | | | |
|---|---|---|---|
| PP12,299 P2 | 12/2001 | Jepsen | |
| PP14,714 P2 | 4/2004 | Vlielander | |
| PP15,509 P2 | 2/2005 | Jepsen | |
| 2006/0130191 A1* | 6/2006 | Jepsen et al. | 800/323 |

OTHER PUBLICATIONS

Britton et al. (Britton et al. 2008. Agrobacterium: From Biology to Biotechnology, pp. 523-563).*
Guo et al (2004, Proc. Natl. Acad. Sci. USA 101: 9205-9210).*
Christiansen et al. 2008. Plant Cell Rep. 27:1485-1495.*
Furner et al. (Nature 319, 422-427 (1986)).*
Nemoto et al. (Plant Signaling & Behavior 4:12, 1145-1147; Dec. 2009).*
Christensen, B. et al. "Transformation of *Kalanchoe blossfeldiana* with *rol*-genes is useful in molecular breeding towards compact growth". Plant Cell Rep. 27 (2008), pp. 1485-1495.
EP Office Action, EP Patent Application No. 13180898.2, mailed Sep. 25, 2015, 5 pages.
Christensen and Muller "The Use of *Agrobacterium rhizogenes* and its rol-Genes for Quality Improvement in Ornamentals", European Journal of Horticultural Science, vol. 74, No. 6, 2009, pp. 275-287.
Lutken, Henrik et al. "Inheritance of-genes from through two generations in" Euphytica, vol. 188, No. 3, 2012, pp. 397-407.
Christensen et al "Biomass Distribution in *Kalanchoe blossfeldiana* Transformed with rol-genes of *Agrobacterium rhizogenes*" HortScience, 2009, pp. 1233-1237.

* cited by examiner

*Primary Examiner* — Anne Kubelik
*Assistant Examiner* — Charles Logsdon
(74) *Attorney, Agent, or Firm* — Casimir Jones S.C.

(57) ABSTRACT

The present disclosure embraces *Kalanchoë* interspecific hybrid plants, and considers rol transformation in *Kalanchoë* species and hybrids. Disclosed herein are methodology and the like for producing rol-transformed *Kalanchoë* interspecific hybrid plants, as well as resultant rol-transformed *Kalanchoë* interspecific hybrid plants with novel phenotypes.

5 Claims, 3 Drawing Sheets

Figure 1. Simplified graphic of the Ri-plasmid (Badstueber 2007)

SEQUENCE LISTING

<160> NUMBER OF SEQ ID NOS: 18

<210> SEQ ID NO 1
<211> LENGTH: 19471
<212> TYPE: DNA
<213> ORGANISM: Agrobacterium rhizogenes

<400> SEQUENCE: 1

```
tggcaggata tattgtgatg taaacagatt agatatggac atgcgaagtc gttttaacgc      60
atgctttatc gaatataaaa tgtagatggg ctaatgtggt tttacgtcat gtgaataaaa     120
gttcagcatt cgtttaataa tatttcaata tcggtgtcta gagaccgtg gatttgtata     180 gtcagcacca tgatatgaat ctataaaata ttgtatctcc aattgcaatt caatcgatat     240
aagaaattaa tacaagccgt tcatatagta aggttgccaa tggcattcaa taacgaccgt     300
acagttgccg ctatattaat ctacgtgcca tttcttaaat aaagataggc gaatgactat     360
cgaaaataaa acaattatta atgagtgaaa acgtattgca caaataaaga ttcattatgg     420
ttggctcaaa ttttggctct ggtgctcgat gacgtcgaga tgaggacagt agtgatcaac     480
ttggcggtcg ataccttggt tacgccactc ccagagtgcc atgtcgtcct ccgagcggtc     540
tgagataacc cagtcggcaa ttgctgctgc attgccgggc gttccccaac cacgacgaat     600
atgctttcgt tcatctaact cgcgtcgcac tgccctccca gtcatgaagt caaagccaaa     660
ttctaccctc tctccatttc ccagctcagt cgagaaatcg taacacctcg tggcagctga     720
cagtttcaga aaggggcgta tccctcgaac tccaggtcc tctttcacat agttagcaag     780
gcgtactgct gcataatctg cgttgaaggc tctgatgact acaggatcct cggacaagcc     840
caattgatca gggcgaaccc tcgcgctcat aaatatgaatt gcgacgaccc ttgcttcctg     900
tcggagcatc gaatcaatcc aagccttccc tgcggcatag aggtcatcga ctgcgatgtc     960
atcaagatcg agtagctttg ccaacctagg aagttcttga ggaaaaatca ccggcatgac    1020
agcaaccgtc tctcgccagt cagttgccgg actggcttcc ctaacgccat ccacgaatgc    1080
ctcaccgctt gcgtatttga atgtgtaaaa gagaaggacc actctttggc ggtacttcgg    1140
acgccggctt agccacgcgg caataatgtg ggcctcaaac tcacgaccat ccaaaaatat    1200
```

```
agtcgcgcct ggattgacct cgctggcctt gtcgagaaga ggttccaaaa agggaacggt    1260
gtctttcgta atagtactta aatctgtgag ttcgccatgc gaaacctctc gaacgattat    1320
cggcgtatcc ctgacatcag ctgaatgaaa ttctcggacg agtttgtcgg gcaaagtgga    1380
gacccgccac gtgttgaagt cgtgggaaac gatgggcaca tcgtcgccgg tgagtgcggc    1440
atcgagctca gagaggttcc gcctgccaac ctcaccgaga gcagctaaca acgaagtttc    1500
ggtgcattcc tgtatccctt tacccagatt atacatgccc cggtgttcga taacttgaag    1560
aggcagtggc tcctcaagat gttcaaggag gtggggtaca gagtgccggg cgaggacctc    1620
atccaccgtg acaccaaccg ggagatccca ttcgagtttc cactgggggcc agcatgtgcc    1680 cgcgacggcg aaaggtttgc gctggcaaag aacccggctg ctgcaggtgg acctatcctt    1740
acccatggca atggggtttt gctaaaaagt caggcacttt actgggcaat tgataggtg     1800 ggattgcgtt attaactgtt ctccagcggg aatctttatc tttattgaaa tgctaaagca    1860
cttagataaa atacagctgt accgcaatat aaaatagtag ataatgtaa tatgtgtatc     1920 gagaatacga caagctaata taatctagcg tcaaattgca ataatttaaa tcaaaactac    1980
tgatgaaata ataaagatg gtcaattttt attggtagga gttgtcgaaa gattcgacgg    2040
acggccatta caatacatag gtgcaagaag taaaacagga agggaaacgg aaaacagtgc    2100
tataaaaaag cgacagatcg cggcgatcac tgactgcgat cgggaagaag ctcgccaagt    2160
tcaccgagaa tagcagagag cgcatcctca tcgggtacta cgaacacatt cgtcccagag    2220
ggctttgttt cagctgcgcc aacccagaaa gcaaggccat tttccaagtt gccgatggcg    2280
gtcagcatgt tttgattgtt gctgccgttt ccacaagcga tgtgaaggcc gatcccgtga    2340
gagaggccct tgacgaaggt gaaatagcct ttggattttc caactgtttc aacgggcact    2400
agatattgac cctctggcgc ggcaaccacc ttgaatttgc gagatgactg gttgccgatg    2460
agcgaagaaa gcatttctcc ggcttctttg taagatttgt gagattccca catttgacag    2520
ccgtagaaat gccccatcgg aatgttgcgg attcccggga tgccaccaaa tttgttctcc    2580
atagccgcgt gaacggcttg ccagttgggc agggagaaag aatcgaagcg atcatctttg    2640
tagatcgtga ccattccatc atttccctgg aatccgatat tttcaatggc gctgaaaact    2700
gaccttgcga tttcttcgca ttcccgtgcg gatgtgagca attgataatg gcccttgcag    2760
gcgatcctgg tcaaattggc gatgatgttg atggcaggat taatatccca acactggtga    2820
tttcgatctt gcttaaaggt ggtaccatcg ccgtcgaagg cgagcagggc ccggagagat    2880
gaatcggcaa gactgcgtcg gacccgctcc gcggcgtcgg gaatgaggct gataagagac    2940
atatccaaag gtgtttgtgg gtaacgggct gctcaatgaa gccttaaatg caacgcaaca    3000
tatgtaagga tgagttgact tattggagag agaaatagga atgagctggc cagccattat    3060
caacgtgggg ccatgctgac aatgtttacg tgaaaggctc aactacctcg aagcagacct    3120
ctatattcgt tgactttatt actgaacaag aagttgcttg ccactcattt tcttaaatct    3180
tgcccttcct gcgcctcgct atcatgcccg ccaacgacgc gacatgcgct gccgcgattg    3240
ccttccccga gggcaactgg aaggaagaac ttgatgcgct ccgcaccttg tgtgaccccg    3300
tcgaggtggt taaggtcgca gtcggcagag gtcttagcgg catatgtaat gttgttgcag    3360
caatgaatcc cacaaaggtg aggggcctcg gcgatgtcat cgggcagatg ccggctctta    3420
atcaccgtat tgctgccgcc gccggcgaaa ctccggtgcg agaccttgga ataggttacc    3480
agtgcgcaat ctgccacccc gacatagcca gtgcgatgtt agccacttct gaggggatca    3540
gccacgttct ccgtgaaagg attgagaaag aagttgaccg ggacattgga gaaggcgcca    3600
```

```
ccgtctgcat tttcgttcag ccgagaatga gctccaaggg ctctccagtt tctgtccatt   3660
tcaccctcca gtttgcgaga tctggaactc ttgtcgatgc cagaatgatg gagagttaca   3720
atttcatgaa aggcaatggc acagtgaccg caccggattt gaaaagtcat tggaagaagc   3780
acggtattga caggccaggc ccacgtccgc ccacgtccaa gtttgaactc ctcttcgccg   3840
ctgtccccga caacagtaaa cttgccgcca ccgattttac ccatctcggc cctgtcgagc   3900
gtgataagga actactcggc agcacggtat tcgggattgc cgctaagaaa cctggtacga   3960
tcgtttatcc gtgcgaaaag gttctctgtt tggaggtcga cgtacacgcg catcgcgccc   4020
tagaagtact tcaccgcctt ggggaacagg cttatagcaa tggccgtggc actagcttcg   4080
gtcttcacac cggtccgtcc tcttgcctta atctttccgc cgccgcgctc gctacatttt   4140
tcaaacgctc ggatctctgt tcccttccat tgagtgatgc ttttgtcctt ttctgcgacc   4200
cgccaccgcc tacagcgcca agaaagatgg ccttccgatc actgccttct cccccacgag   4260
caccaatcag ttcgaactcg tagagcctca ggtcgtcaag gcatatgttc tcggacttt    4320 cgacgcgccg acgatggtta cgccccgcga caaaacgcga gccagcttct gcagccaata   4380
tgtacgtttc cgtgaaccgc atccctgtga agagttcaat gaaattggag ttttgatcct   4440
cgatgctgct gctaaaatgc tcgaacgtta tgcaaaattt ctagaagatg gtggaagaga   4500
tgatgatgaa atggcgaaca taatagatgt atttgggttt tgtcttaact agtggattga   4560
ttgaaacaaa ggagtccgag ttgggattcc ctttcggtct tcgtcgtgca acgatatcgt   4620
atgcgtacag gtatcacatt taacgttgct gcggcggacc gagcccgctt ggaagcgatt   4680
gttgcagctc caacttctgc tcagaagcac gtgtggcgag cgaagatcat cttgatgagc   4740
agtgatggct cgggaacggt cgcgatcatg gaggcaaccg gtaaatccaa aacctgtgtc   4800
tggcgctggc aggagcgctt catgactgag ggcgtcgatg gccttttgca cgacaagagc   4860
agaccgcccg gcattgcgcc gcttgatggc gaactcgttg agcgtgtcgt cgcactgacg   4920
cttgagacgc ctcaacagga agcaacgcac tggactgttc gtgcgatggc caaggccgtt   4980
gggattgcag cctcttcggt tgtgaagatc tggcacgagc atggtcttgc gccgcatcgc   5040
tggcgctctt tcaaactgtc gaacgacaag gcctttgccg agaagcttca cgacgtcgtt   5100
ggcctctacg tctcgccacc ggcccatgcc attgtcctgt ccgtcgatga aagagccag    5160 atccaggcac tcgatcggac gcaaccggga ctccccttga agaaagggcg cgccggcaca   5220
atgacccacg attacaagcg ccacggcacc accaccctat tgccgccct caacatcctc    5280 gacggctcgg tgatcggccg aaacatgcag cgtcaccggc atcaggagtt catccgtttt   5340
ctcaacgcca tcgaggcgga actgccaaag gacaaggccg tccacgtcat tctcgacaat   5400
tacgcgaccc ataagcagcc gaaggtccgc gcctggctgg caaggcatcc gcgctggacc   5460
ttccacttcg tcccaacatc atgttcatgg ctgaacgccg tcgagggatt cttcgctaaa   5520
ttgacacgtc gacgtctgaa gcacggtgtc tttcattccg tcgttgacct ccaggccacc   5580
atcaaccgct tcgtcagaga gcataatcag gaaccaaagc cgttcatctg gagagcagat   5640
ccagacgaga tcattgcagc cgtcaaacgt gggcaccaag cgttggaatc aatccactag   5700
cgtatgaaca gtaataagaa aatcccgatt gtgaatagtc ccaatttcaa atgtgtccgt   5760
gtgtaatttg cgtgtcttca gttgaatttc ctttaataat atcaaatatt caattgtgaa   5820
aagttgtatt ggttcaggtt caagcttccc gaatttgttg aatttttattc cctgttttca   5880 atttgttgac ttgtttggga gacaccttt ttgtgtttcg tgaacatgtc acccctcgg    5940
```

```
tatacattag cctacaaagt aaataacgtt gataaatgtc actcatgttg taataaaatt      6000
gagcttatta tgtataacca gaccctgtgt taatctaatt acaaagaaat tcatcattct      6060
cccaagcaat cctgagtagc tgcgtgatgg atcttccata tcagcgccca cgtttcaccc      6120
cgtttgccgt cacccatcca cgtagtggag tcaacctgaa ccgtgcaatt tctcaggcct      6180
ttgtctgcta tgatcagttc tgcgaacggc tcttgcgata tcagcaaagc tggacggatt      6240
gggtgttcga ccacggattt gcagaagcca ttgaagacgt ggcgctggtg ttccaggttg      6300
caccttgcct tcatggcccc cgaataggcg cgctcgaagt gttgatacct cgtcgcaccc      6360
aggtcttcat ttatatgtcg aacaaccaat tgcagcgctt tgttcacac cagtgcattg       6420 ctcaacttgg cgacgccgtg cttgcttgca tgatcccgcc ctacgcgagt gacctctcgc      6480
tgcaggaaat ggctcgggcg cacaacagat tttgcccagg cagttacacg aggtccgcag      6540
acgtacagtg ctttatcgcc atccaactca gcagccgatt cgttgaggag gcacatgta      6600 acgtgcacgg gcgaaatggc ttaaaaagaa cctgccgctt ctttcgtcgc cctgctgagt      6660
tcttcagccg ttatgacatc gttgccattg gccggtgct cttccatgat gaactggatt       6720
gcccagcaaa ctgcaatgag cctctttcct gctttgacct gcggtacgac tatcaggttt      6780
tcctccagga gtgcgatgcc catgatggtg tggggcatta tccggaaggc gcaccactac      6840
ctagtgttgc catcgtagga ggcgggctgt ctggccttgt tgctgccaca gaactacttg      6900
gcgctggcgt caaggaaatc actcttttcg ataccgttga tgagatccgt agttttgggg      6960
catcgccgat gccaaacggc gacgctcacc aggccttgac gtcgttcggt gtcatgcctt      7020
tctccgccaa ccaactttgc ctgtcatact atctggataa gtttagaatt ccgtccagcc      7080
ttcgttttcc ttgtgccggc aacgaccaca cagcactata tttccgccag aaacgctacg      7140
catggcacgc ggggcaagct ccgccgggga tatttcagcg ggtacatgtc ggatggaaga      7200
cactactcta ccaagggtgt gaacggaatg gcaggagact gatggctccg atggatatct      7260 cttcatgtt gaaagagcgt cgtcgtgatg aagcctcaga agcacggcag ctttggctcc       7320
gagagttcgg aaaattcact ttccatgccg ttttggtcga gatcttcagc tgtggtaatt      7380
cgagtcctgg tggcaaggca tggcaaacac cccatgattt cgaggctttc gggatactga      7440
ggttgggata cggccgagtt tcgtcctatt acaacgtgtt gttttcaacg atcctggact      7500
ggattatcaa tggctacgag gaggaccagc atctttctat tggtgggtt caacttttgc       7560 aggctctgat gcgcattgaa atattccaga aaagccatgc gaaagcacga ctctgttttg      7620
atcccgtgcg tggaatagcc aaggagggcg ggagattgaa ggtatgcttg aaacacggtc      7680
attcgcgtgt ttttgaccag gtcatcattg gcggcagtgc tgaggccgct acagttgata      7740
acagactggc cggggatgag acttccttca gctacaatat cgaacccgcc gtcggaaact      7800
cgtctgccgc tgtcaattca gcactcttca tggtcacgaa gcaaaagttt tgggttaact      7860
ccggcatccc agcagtgata tggaccgatg ggcttgtccg tgagctgtgt tgcattgaca      7920
tcgaatcgcc agctggagag ggccttgtcg ttttcacta tgctttggat gactatctat       7980
cccggccgat cgagcatcat gacaagaagg gacggtgctt ggaattggtc agggagcttg      8040
ctgctgcctt tcctgaactg gcttgtcacc tggtcccagt caacgaagac tacgaacgat      8100
atgtcttcga cgaccaccta acggatggtt ttaagggagc tttgtggagg gaaaattctc      8160
tggaaaaagg tcagtatatc caggatctgc ctgggaataa ttttcctatt ggggatcacg      8220
ggggagccta tctgattgac cgtgacgact gcgtcaccgg agcctcgttc gaggagcagg      8280
tgaaggcggg catcaaagcg gcctgcgccg tcatccgcag caccggcggg acgctctctt      8340
```

```
cactccaacc ggtggactgg aataaaaaat agaaatttcc tgattaagtt atagtcaatg    8400
tactattgcg tgttaatccc gtaggtatgc aagctgcacc ggcagcatca taatttgatg    8460
ttccatcaat aaattaaggt gcccgttcat tgtgtattac attatgtatg tttatcaaaa    8520
atataatcga agtccatttt aagtctgata ttaattggaa ttccaaacga ttccttgatg    8580
cctatcttcg ctatgattgt atggtaataa agtctccaca tctcccgaaa aatgctttcg    8640
tgatttactt gtctctcacg tgctttcgca tcttgacagc caaaagtggg caacttgaga    8700
agagtattaa ctggccacgc aactcgagat attcccacta accccaatga cgtcattgca    8760
ctcgtcacgg gtagcagccc cacttgcctt tgccacttta ttaattcttt ggcccactgg    8820
ccattaattg gcacctacat atattagtgg agaagataaa gtgtcactat cgtttcctgt    8880
tcaattttga attttgcaag gatttcatgt tgtcaactac acagcttgaa aggaaatccg    8940
caatcaacgg agaaacgtca acatctcgac aaaaaaagaa tgcttcatca ttgcgtagac    9000
tgcatattga ccgctccttt cggcgctggg cctgctttta ctgttgccta gcgttcggac    9060
agccaccaga gaatgggcta tatagatcct ttcatcaaac caaaacatta ctaagatcat    9120
gctgtaacgc ttcaatacgg tgagtgtggt tgtaggttca attattacta tttttgaagc    9180
tgtgtatttc ccttttttcta atatgcacct atttcatgtt tcagaatgga attagccgga    9240
ctaaacgtcg ccggcatggc ccagaccttc ggagtattat cgctcgtctg ttctaagctt    9300
gttaggcgtg caaaggccaa gaggaaggcc aaacgggtat ccccgggcga acgcgaccat    9360
cttgctgagc cagccaatct gagcaccact cctttggcca tgacttccca agcccgaccg    9420
ggacgttcaa cgacccgcga gttgctgcga agggacccct tgtcgccgga cgtgaaaatt    9480
cagacctacg ggattaatac gcatttcgaa acaaacctac gggattaata cgcacgtggc    9540
tggcggtctt cgattcattt ccacgccgga gatgatatcg aatatgttct gttaagttaa    9600
aataagctgc gagccatggc gcgattgtcc tgttttatta atatagtact ttaacgtctc    9660
tttagagcgt ttgtgtaatg tcgtgaaaat gtttatgtc aaatgtactg ttgaactata    9720
atattataag tccaggtgtg tcgttgttgt tgatactgca atatatgtgt agtagattag    9780
atagtcatat gagcatgtgc tgttttttggc aaaattcagc agcaggatca acacagaaga    9840
aaatatttag tacaagaaaa taggtcaaca cattacaacg tacgctacaa ctcccaaggt    9900
tctgtgtcac agactgcggg agggtacata gaacttatga caaactcata gataaaggtt    9960
gcctgcaggg ggagttcaag tcggctttag gcttctttct tcaggtttac tgcagcaggc    10020
ttcatgacgc cctcctcgcc ttcctgatca ggccccgaga gtcgcagggt taggtctggc    10080
tccggtgagg aggcggccgg acgtgatatc ccgagggcat ttttggtgaa ttgtgtggtg    10140
ccgcaagcta caacatcata ggggcggttt tcagtccctc gccgcagaaa gaaggtgcaa    10200
gctacctctc tcccgtaaac gttggtcact tttaactcca gcaagtgaat gaacaaggaa    10260
cttgcgaaaa tggcgatgaa gcattctaaa tcaggttcct ccgtgcggct gtgcggcaa    10320 gcaaggttgt gaacacggag catctcctgg agggcgagct cgctccgata tggttgaatc    10380
gttgtcgcca gcacggcctc cattccaaat gtaatggatt gttccttcag cactttctgc    10440
atcttctcgc gagaaagata gacaaataca tgttggtcgt tttctcgagc cagatccggc    10500
tgactaacaa acataggagg atgatagcag actttgttct tcaagagctc agctagttgt    10560
ttaagtatat atatcggtgg agagttttcc ttcaaatcta gcactgcaag agcccatcgt    10620
ttctggaaat gcaggagggg tttgctatag tcacggctat agattgcaaa agcaaatcgg    10680
```

```
atcccctcga ataggtttat ctggctccat gctggagtga gatctactgg ttgaaatcgt    10740
ggaaggaata gcaatttggg atccattgtg atgtgagttg atagttacg aaaaaggcaa     10800 gtgccagggc catttaaaat acggcgtcgg aaactggcgc caatcagaca cagtctctgg    10860
tcgggaaagc cagaggtagt ttggcaacaa tcacatcaag atcgatgcgc aagacacggg    10920
aggccttaaa atctggatca agcgaaaata ctgcatgcgt gatcgttcat gggttcatag    10980
tactgggttt gcttttctt gtcgtgttgt ttggccttag cgaaaggatg tcaaaaaagg     11040
atgcccataa ttgggaggag tggggtaaag cttaaagttg gcccgctatt ggatttcgcg    11100
aaagcggcat tggcaaacgt gaagattgct gcattcaaga tacttttct attttctggt    11160 taagatgtaa agtattgcca caatcatatt aattactaac attgtatatg taatatagtg    11220
cggaaattat ctatgccaaa atgatgtatt aataatagca ataataatat gtgttaatct    11280
ttttcaatcg gaatacgtt taagcgatta tcgtgttgaa taaattattc caaaaggaaa     11340
tacatggttt tggagaacct gctatagata tatgccaaat ttacactagt ttagtgggtg    11400
caaaactatt atctctgttt ctgagtttaa taaaaaataa ataagcaggg cgaatagcag    11460
ttagcctaag aaggaatggt ggccatgtac gtgcttttaa gagaccctat aataaattgc    11520
cagctgtgtt gctttggtgc cgacaggcct aacgtggggt ttagcttgac aaagtagcgc    11580
ctttccgcag cataaataaa ggtaggcggg tgcgtcccat tattaaagga aaaagcaaaa    11640
gctgagattc catagaccac aaaccaccat tattggagga cagaacctat tccctcacgt    11700
gggtcgctag cttaaaccct aataagtaaa aacaattaaa agcaggcagg tgtcccttct    11760
atattcgcac aacgaggcga cgtggagcat cgacagccgc atccattaat taataaattt    11820
gtggacctat acctaactca aatattttta ttatttgctc caatacgcta agagctctgg    11880
attataaata gtttgatgc ttcgagttat gggtacaagc aacctgtttc ctactttgtt    11940
aacatggctg aagacgacct gtgttctctc tttttcaagc tcaaagtgga ggatgtgaca    12000
agcagcgatg agctagctag acacatgaag aacgcctcaa atgagcgtaa acccttgatc    12060
gagccgggtg agaatcaatc gatggatatt gacgaagaag gagggtcggt gggccacggg    12120
ctgctgtacc tctacgtcga ctgcccgacg atgatgctct gcttctatgg agggtccttg    12180
ccttacaatt ggatgcaagg cgcactcctc accaaccttc ccccgtacca gcatgatgtg    12240
actctcgatg aggtcaatag agggctcagg caagcatcag gttttttcgg ttacgcggat    12300
cctatgcgga gcgcctactt cgctgcattt tctttccctg ggcgtgtcat caagctgaat    12360
gagcagatgg agctaacttc gacaaaggga aagtgtctga cattcgacct ctatgccagc    12420
acccagctta ggttcgaacc tggtgagttg gtgaggcatg gcgagtgcaa gtttgcaatc    12480
ggctaatggt tagtcgatgg gctgacgagt ttgatgtcag gagaagctga gtgtgtcact    12540 tgtttcccctt taagaagtat taatgtaata aaaatcaaga tctggtttaa taactggata    12600
cttgatttca tcgcgctttt tttgaataaa tgtttgttgt cttgacttta agatatcctt    12660
tgaaatttgc gttattcgta tttcgctttt ggttatttcc aaaagacttt gctcagtaag    12720
atcaaacgtt tgtatttctc cgggccacaa tatttgacct atatgcactg gcccacgcgc    12780
cgcaatagat gaaaattgcc aaaattagct atcggtcttc tgaaaagaag ggccgacatg    12840
ttttcataga ccatgcaaag tcatactacc tgaaactgat aaataacgac aaagaaagta    12900
gcctatttaa aagtcgctat agcatgaatt caacacaagg aaaccaaaag tcggaaggaa    12960
gactttaatc ccggattatt tggacatgat aggagctatg gggcaacgtg tcattttcat    13020
gagtgttgaa tgattttctg tagcaaatag aaaacgtttt ttaaaacgat gtggccttgg    13080
```

```
agtaatcagc ggaagaaatg gtcatgctca gataatttcc gttgctgacc tcgcaaccaa   13140 ccccttaaa  tacctctgct gcccatgcat tttgccaagt taacctaaag tggcagctga   13200
atggctcgtt attgcagtgg tggctctcaa cggcttcatg tcgatgattt tcgttggatc   13260
aaggagccca ctcgactgaa ggctcagctt attaatgtgg tggagaccta caaggctgca   13320
caaacagaga cgttaaagta ctatatatca tctgcaactg agcgtgtggc tcatgtggag   13380
gcagccgagg tcaacaatgc ggaaatggag ctgcatcctg ctgggttgaa gtaccctctg   13440
tccttcgtct ttacctcct  ggccgtggct acagcctgca aggagaacaa gcatctcttg   13500
tgcgaggagc atttggaggg ggacttgata tcgtgcgtcg ttcctcccta tcagacaaat   13560
gtctcactcg ctgctttaag ggagctccac aattccattt cgggaggagg gtaccaggaa   13620
caagcagaca tggattattt tgtggcgatc atcccaaatg ataatttcga ctatcagagc   13680
tgcgaaatcg acacacgaag ttgcggtaaa ggactttgca agatttatag tagggaactg   13740
ggagggcagc tctagctta  tgacgccata ctggcaatcg gcaaggtgct gctgctggaa   13800
tagatagtgg gccgctgatc cgagtttgat tttgtcgtat tatgttacgt gaacttttta   13860
tcatgcatgt ttcgcttatg ctcccgagtg tcggccatgt tgttgtgtta aaataaaagg   13920
ctgatgttaa gtcctattgt aaaataccct tatagattaa atatatatag tataacttct   13980
gtatgccgtc gatgagcggt tatatgattg taatctatac gttgttgcaa tcaatcgtat   14040
tacagtgagc cgtgcttaat gaaataaaca tcatgttaaa tgtctattta ttcaatcaac   14100
atgcgctgac aataatcaaa aggggaaacg taataacatt gcggtggata cagcgtttat   14160
tgggaggtcc gcgggccgat acacttaaat aacatagaca gaatttgaga gagcacgcag   14220
gttgtagcca agttgagcga cttgccggta gcacggaagc taagctcagg tgttacaaat   14280
agacaggcgt cgaggcgacg agcacgacga ccttgccgga cattgcggtc gcaggggct    14340 caaagcggtt ggcttgtaac ggaccttgtg tttcttgttg tagctttcat cgagcataac   14400
cattgggacg gttgctgaac aacggtaacg cacttttttc acgggagcga ggtagaagaa   14460
catatttccc cgtcggcagc cggcggtgag catgccaatt cctaagggat caatggactc   14520
gtgcgaacgg tgagcatgcc gttctgaccg tcggtgccca atcagcaggc cactcccaac   14580
atgttttcca agtccttaaa accagtcttt atagcattga tctcccagca atctttattg   14640
aagtcgattt taatattcaa aagaagattt tagtggaaag ggaatataat cgcgtggccg   14700
aagaagagcc ttcaaaaatc agaatccact aggataaaca ataatatctg aaaagcattg   14760
aatttgggtt aggcacgaga ggctgacgcg gatgccactc gattgctagt ggaaggattc   14820 cctttttct  agcgtatcga attcaccgtt tcactatatg ttttcctgat tggttgatct   14880
gcgggaccac cattgactgc cactaatatc gaaagtgggt ctgcttcgat tatgatgctt   14940
tgtgagaggt tctcttccca atgcatgcaa gctggcagat tcggatactc tcaatagaga   15000
tcttatttcg cgtctcaaaa agttcccaga aatcaacaaa ggggagggca ggtcctttaa   15060
atacgttgca gctgtccttt aaaatagaag agaatttaca gctggaggca cagaccacta   15120
aactgcgaaa gtaagcatgg cagatgagtt ggagcgtcaa ttggaagcca tttctctcat   15180
tacagtcctg ggtccggatg tgaaggctga gcttgaggcg gagctacgag actactgcga   15240
agatctcgac ttctggaaaa gccacggttt accggtggcg gatctcgatc agactgtgac   15300
tgtcgacaag cttctataca tgtatatgga tcgggcaaca gcagacctgt gtgtgaagaa   15360
tcgctgcctc gtttgcaaca gtggcaattc agccgcaaaa gtaacctcgc ttccaccata   15420
```

```
ccttgcaggc gtgacaagcg ccgaggccta tgagaaactc aactccattg ttgatgggag    15480
tgtcgccccc caatctcgtg ggcctccctg ctattttgtg gcgttcctgc ccagcagctg    15540
tttcgagaaa accagtgaga tatcggtgcg cacagtggac ggcgagtgtg gcccttcga     15600 tgtctttacc cggcagcgtc agccacagga tcagagtgat atgttttta aatatgaagg     15660 agttgtatgt gctggaaaga gtgtatttat gtaagaatta tcttttatag cctgtgttac    15720
gtttgaaccc ggtccgcgcg gtattgtttt caataaatgg tatgtgcgga ggatataatt    15780
ggtctttcat tggtgtgatt tacgtgtaac gcggataata ataaagtaaa ttacaaaaga    15840
gaaacgcata attttattcc agaatgattg cgagaaacga tgaaaataca tgaaaatgca    15900
tattgtcgcc agggaaggat ggcgccgaaa taaacgaaac tgagccaata cagtgacttg    15960
ccaagcgagt ttgatcctac caaattcgcg caaattaatg cccgtgttcc atcgggccag    16020
cgagtttatt caaaagagtt tcgtacacgt gggcggcgac ggcaacgtca atgcttgcta    16080
gccctaccgg cgagaagttg gccggcccct tccatgcctt gaggtcattc atcaaggcct    16140
cgtcatcgag aatttcggtg tagttcttga tcccatcgcg cttgccgtgt tgggtcagtt    16200
tcataccgcg cctagaatag tagagggcaa cggcatcaac gttgcgggct tccatcgcaa    16260
caaggtcatc ggcgacaatt agaccatccg cagataggac atgctcaatg taatccggcg    16320
gcatgtcatc aataccgagt gacaaagtga ctgcgttggg ggcgatttca gcggcttcga    16380
ataccggttt tccgtagttg gtcgccatga tgacgaattg agaatatggc aaaaggctac    16440
gatcgccgac agcttcaagg ctaaaggtta cgcaatcacg taacttttcg acgagctcga    16500
aattggattt cttaccgcgg ctgagcactg ctaccttacg aattctctta gcggcaccat    16560
agttaagtga gagaattaca gcttcggcaa cttttccagc cccaaacaag aaaacgtcga    16620
tgtcctctct gccttgcaac agcaggttta cgcatgctag cgagaaccaa cccgttcttc    16680
cattagaaat tgccacgccc tctaccgaca taaggagcgt cccggacacc ttgtcgcgca    16740
ggaaaatatc ggagtgctgg agcggctttc cggtagcggc gttggttggc gcgaagtgga    16800
tgtctttggt gccggaatat cttccgaaat agccaatgag tgctccttca gtccatccag    16860
gaacattctt gttgaacgtt aggtaagctt tgacatgtcc ggcttttcct gcggcaaaca    16920
cctcccaata ggacttgaga gcttcgtcaa caaatgctgg tgtgatctgg atatcgaggt    16980
ttgatagtgc agattcagtc cagtgtacct cgcaaagttg tttggccatc tgccttgtag    17040
gtgcgaattt tctctgctca aattgttgag gttagcggat ttgtaaacgc gtttatatgg    17100
gctgcttgga gggtactttt ggattaattt ttttctgcca gcgcattctg acgcggcacc    17160
gctttggaaa gtgcgctgtg ggtccgcgtt ttctacaata atgtgccgat ccggtcagaa    17220
agtatatgga tgagttgtgc cagcctcacc aacgtgctgc aggcccatca tgactacttc    17280
aatgttaatg ggggtaatga ataaataggc gaaattgggt tcacggtggg cccagggaat    17340
ataatattgc cgcagaggta gtcggatgcc aaggcccgca actaatagtt cacgaacaaa    17400
ttcattgtag tgggcggcca actccaaaac caattgccag ttattgtatt gcaatacata    17460
tatgagtatt cggatacaac taatttcatt aaataatatt ttaagtgtgg acagaatagc    17520
gcctaataaa tttgcgaatg ttgtccaatt gacgttttta taggtaactc gataaatcgt    17580
gcttttgtga tattctgatg cggacaatat acatttaaac ataaagatat aagttattga    17640
ggcatttatg tatattacaa tagtgggta cattttcac agatgctgtc acccatgaaa     17700
tattggcaaa atactcttaa aatatgcaag aaactaaaga ggatgcatgg gttgggctgt    17760
aggtacatgg atgcaaatgc tgttttgcaa taagtcatat agtctcgtct gttgagtgag    17820
```

```
gcccattcaa tcagcaagta ggactgaggt gcatgatcga catattttg aaccacagtt    17880
ttggcaagtt tttcatacaa atgcacggct acggccaaat cgtagcttgc aagtccaact    17940
gctgaaaagt tagccggccc gttccaagaa attagccttt gcataaggac tggatcgcgg    18000
agaacttcag agtagttcct gatcccattg tccctgccgt gttttgttag ctttaaatgg    18060
cgtcttgaat agtgcagcgc caacgagtcg atattacgtg tttccatcgc atccatatca    18120
tctgccacca cgatgccact cagcttcaac acgtgatcaa aatagtcagc tggcaattcg    18180
tcaattccaa gcgtcaatgt aacggcattg tctgtgatct ccttcatctc aaagacgggc    18240
ttgtttgaat tcgtcgccgt aattatgaac ttggatttgc tgagatatgc tcgattgtta    18300
acagccttga gtgaaatctt gacttccggc tgaagccttt gcaccaactc atggtttgac    18360
tggttgcagc ggctgagaat cgcgattcgt tgaattcttc cagatgctcc cgaattgagg    18420
gcgaggatga tggcctcggc aactttacct gctccgaata ggaagacatt gatctggctt    18480
cggccctgca ataggagatt caggcatgct agtgccagcc aaccagttct cctctccgat    18540
atagccaccc catcaacaga aagagacgt ctacctgtga acgattgcg aagccaacgt    18600
cgatgtgaga agtcggttct ttgtatctcg cgtttgacgg attagaatgg atgcttttca    18660
caccgaata gtcgccgacg aaacccacca gagctccctc cgtacagccc tctcgatcaa    18720
gtggaacgaa gaccttgttg tggccgagcc gcccttcagc aaagaggtgc aataatctt    18780
tcaaggcatc cgcgacgagt tccggtgtaa tgtatattcc aaaagccgat agagattcct    18840
ctgtccaaca ttgctcgtgt atttgatcgg ccatgtttgt gtttgatcag cctcctttcg    18900
aaaatttctt gagtttcgaa taattctaaa atcgaaggac gattaatagt gccataccaa    18960
gacaagaagg gtaggtgggc catcaatcca caagcctagc acattttgct gtctgctcat    19020
gcaaggtatc caatggaagc ctggattggt tagccgaact tggtgggttc aattggagcg    19080
ggcaggtcac ttttgtctc tcaaataact gaaactaagt tttgttattt ggtatgtgtt    19140
tgtctgttct gccgaaggtg cccgaatttg cgcaaattcc tttctaaaaa ggcttacatc    19200
tagcaaaagg tgagccctgt gcatcccagc atttggacaa agcgcgccaa ttcggacagc    19260
gactggctgc gttggaggct cggatctcaa agaatagaaa agagttatga tcatgttcag    19320
aaccgccaat tttgtgcggt atgagctctt tgatgaaagt aatggtttca aaaagcaac    19380
atcgtgggtg aaaggtacct acatatcttc acagacaata actactgttg ctgtttgctg    19440
attgactgac aggatatatg ttcctgtcat g                                    19471

<210> SEQ ID NO 2
<211> LENGTH: 5995
<212> TYPE: DNA
<213> ORGANISM: Agrobacterium rhizogenes

<400> SEQUENCE: 2
gtcgacagtc gcaacagcaa tcagggggtg ttgatcaacc ttggccagtt gcccttcgtc      60
cctatcagta acgacaacct tgtaatcgcc ggtttccgca agcatcagag caatggctcc     120
gccaatctta cccgcgccga taaccactat ttctttcata caaatcccct gtgttctgta     180
tataggatat ttataaaaat aaccggggat tggtcgaatc atagcggcaa ggtgggcatt     240
atgttatata ttttgtgca aaaagacgac tgcacttggt aatatgaagg ggttccgcat     300
gcaattgacc gaaagggatc gggagctcct gtcgttactc ggcgaaaatg ccagaacgcc     360
tgtggcgacg ctcgcgaaaa agctttctct atccaggacc acagtgcagg ctcgcttgga     420
```

```
gcgccttgag agagagggag ttattgtcgg ctatggtgta aggctatcga atgaatattc    480
ctcgagcttg gttcgagccc atattctgat caccattacg aaggcgcttt cacaggtgac    540
ggcctccctt gggaaggtca cggccgttat cgctcttcat tctgtgagtg gcacttttga    600
tttgattgcg attatcgaag cccttcgat ttcagagctc gatcagttca tcgatcaaat     660
cggcataatt gaaggtgtcg agcggacgct ctcttcgatt attctttcaa cacgcatttc    720
acgctgaaag agcaagaggc cacagccgtg cgcctgctgc cacctttccg acgatgacca    780
tgcagaactt acggcctcta tgtcggtgta ttccacccac cgacgcgcca tttccgtgtg    840
cattaagata atgctttccg ccccatcgga ttgctgttct gacatggtat atcattacga    900
cagccaatgt ttggcggctc gtacgaatca tcaagcggtc aacctgtgct gtcaaccgtc    960
acgatatgag caagcaactc aaacgctttc ctattcaccg cacgcgcgtt gttggctgtt   1020
tggcaggata tatgccaacg taaaaatgag ggcaatcgat tgtactgaat cggatttttca  1080 agggtctggc caaaactatt ccgtgggcac ctggcacacg ccctggagtc cggcccgttt   1140
ccagttgagg gttgtctacg cttagatgag aaggaaagtt gtccaagacg aatcccagtg   1200
tcctattacc aatagccggc gctagtttga tttcagaata agagaaatt cgtcacacca    1260 aatattagaa gcaatgtttg attgaccatc atacttaaga tgaacattcc aaacacagtt   1320
ataatacgca ttattattga cacaatataa aattataatg ttgatattcc ttgaaatata   1380
atattacaat agataaagta gaggaaatta tgtcagaaat ttggtttggc tctgcttacg   1440
acagagtcgg acgatgccta aagtctattg cttcttctat cgctagtcca attgctaaca   1500
gacgttcatc cgagcttgca gagccatcga tttccatgcc aataggcaga ccgttggaac   1560
taagagaaac gggaagactt aggcccggca ggcccgcatt actgctggga tctacattcc   1620
gcacgaagat tttaaggta tcggtcattg agccattgtg aatcaccgat agatcatggc    1680
caattggctt ggctgtcaac ggagctgttg ggaaaagaat tgcatctagc tgatgcgcct   1740
tgaagtaact gtggtaggcc gcttggagtc tcggtctgaa aaacgtcgc gccagacaat    1800 actcgctttt ggaaataaga ttatccgaga gttgtgcatt gagaatactt gcaacatccg   1860
gactgcgaat cgctctgaca acctcagaaa aggaaacacc ctctacgaag ttctgaatat   1920
aatgttcaag ggacaacgga aattcgtaga tggcagtcgg aaagctgacc ccttcattgt   1980
gatgcgctaa atcaggaata tctgcttcaa caaaagtaac atctttgcgt gccagaactc   2040
tgataatcgt ctcggctgct aaggcgacat cgggctccag gtcgttgtaa aagtaagcgg   2100
ttggcaagcc tatacgcagc cccttcaggc ggaccgtttg attaaccggc ggtctcccgc   2160
aaatgatacc gtcaagaaga atcacgtccg gaacattctg tgcgataacg ccaggggtgt   2220
cccgggtggg gcttaccgga actattccgt ccgttggata tcgccccacg gtaggacgaa   2280
accccaccac gccgcacaag gcggccggta acggaccga cgctcccgtg tcagttccga    2340
cgccgcccag catcaatcgg ccggccaccg cggcggccac accccacttt gatcccctg    2400 ggatgagact agggttccac gggtttcgta cggcgcctgt ggcgaagttg ttgctcgtga   2460
tcccaaaaga caattcgtgc atgtttcccg aagcgccagg cagtgcccca ccgcgagaa    2520 gttgtcgtgc aactccggca ggcgtcttgg gtttgtggtt ctgtaagcct ggcgtaccag   2580
cggtcgcggc gaacctgcct gtcgcaatat tcgctttaaa gcataggga acgccagcta   2640 ggccaacacc ggcacctccg tgttgatcga ttttgctggc agtccaccgt aggtgcgccc   2700
agtcggtttc cagaaaggcg tttaaggatc ttgctgcttc acagcgggct attatcgttt   2760
cgattaactc aaagcacgag tatttctttt ccctgagaca tttaagcgtc tcggtgatcg   2820
```

```
aggagagggt caccatttttc gttgtgctga gggaactgag atagatctcg ccagagaaac    2880
gttcaatgat ttttgcttgg agtgaaaaag gcaaataatt atagaggaag gaagtcagaa    2940
atgctgcgca gtagggccac ttgtataagt gccggtcgaa cactgctggt ggaaagtcaa    3000
aagcgtgaag tattagttga actctgttac taaattgaga taaatgggat attttattcg    3060
aaagtactgt ttgagatcta gcgacaataa taatgtcatc ttatgagatt gcatggcaat    3120
atggatctaa tatttggcat aaatagatgg tggttttgtc tccactttta aaccttcaca    3180
gcgttaccct aacacctctt aattgcgtac actcctttca accgcatcaa tggctggatc    3240
ctccttcaca ttgccatcaa ctggctcagc gcccctttgat atgatgctta tcgatgattc    3300
agatctgctg caattgggtc tccagcaggt attctcgaag cggtacacag agacaccgca    3360
gtcacgctac aaactgacca ggagggcttc tccagacgtc tcatctggcg aaggcaatgt    3420
gcatgccctt gcgttcatat atgtcaacgc tgagacgttg cagatgatca aaaacgctcg    3480
atcgctaacc gaagcgaacg gcgtcaaaga tcttgtcgcc atcgacgttc cgccatttcg    3540
aaacgacttc tcaagagcgc tactccttca agtgatcaac ttgttgggaa acaaccgaaa    3600
tgccgatgac gatcttagtc acttcatagc agttgctctc ccaaacagcg cccgctctaa    3660
gatcctaacc acggcaccgt tcgaaggaag cttgtcagaa aacttcaggg ggttcccgat    3720
cactcgtgaa ggaaatgtgg catgtgaagt gctagcctat gggaataact tgatgcccaa    3780
ggcctgctcc gattcctttc caaccgtgga tcttctttat gactatggca agttcttcga    3840
gagttgcgcg gccgatggac gtatcggtta ttttcctgaa ggcgttacga aacctaaagt    3900
ggctataatt ggcgcaggct tttccgggct cgttgcagcg agcgaactac ttcatgcagg    3960
ggtagacgat gttacggtgt atgaggcgag tgatcggctt ggaggaaagc tatggtcaca    4020
cggatttaag agtgctccaa atgtgatagc cgagatgggg gccatgcgtt ttccgcgaag    4080
tgaatcatgc ttgttcttct atctcaaaaa gcacggactg gactccgttg gtctgttccc    4140
gaatccggga agtgtcgata ccgcattgtt ctacaggggc cgtcaatata tctggaaagc    4200
gggagaggag ccaccggagc tgtttcgtcg tgtgcaccat ggatggcgcg catttttgca    4260
agatggctat ctccatgatg gagtcatgtt ggcgtcaccg ttagcaattg ttgacgcctt    4320
gaatttaggg catctacagc aggcgcatgg cttctggcaa tcttggctca catattttga    4380
gcgagagtct ttctcttctg gcatcgaaaa aatgttcttg gcaatcatc ctccgggggg    4440 tgaacaatgg aattccctag atgacttgga tcttttcaaa gcgctgggta ttggatccgg    4500
cggattcggc cctgtatttg aaagtgggtt tatcgagatc cttcgcttag tcgtcaacgg    4560
gtatgaggat aacgtgcggc tgagttacga aggaatttct gagctgcctc ataggatcgc    4620
ctcacaggta attaacggca gatctattcg cgagcgtaca attcacgttc aagtcgagca    4680
gattgataga gaggaggata aaataaatat caagatcaaa ggaggaaagg ttgaggtcta    4740
tgatcgagta ctggttacat ccgggttttgc gaacatcgaa atgcgccatc tcctgacatc    4800
aagcaacgca ttcttccatg cagatgtaag ccatgcaata gggaacagtc atatgactgg    4860
tgcgtcaaaa ctgttcttgc tgactaacga aaaattctgg ctacaacatc atttgccatc    4920
gtgcatactc accaccggcg ttgcaaaggc agttattgc ttagactatg atccgcgaga    4980
tccaagcggc aaaggactgg tgttgataag ctatacttgg gaggatgact cacataagct    5040
cctagccgtc cccgacaaaa gagaaaggtt cgcatcgctg cagcgcgata ttgggagggc    5100
attcccagat tttgccaagc acctaactcc tgcagacggg aactatgatg ataatatcgt    5160
```

| | |
|---|---|
| tcaacatgat tggctgactg atccccacgc tggcggagcg tttaaactga accgcagagg | 5220 |
| caacgacgta tattcagaaa ggcttttctt tcagcccttt gacgtaatgc atcccgcgga | 5280 |
| cgataaggga ctttacttgg ccggttgtag ctgttccttc accggagggt gggttcatgg | 5340 |
| tgccattcag accgcatgca acgctacgtg tgcgatcatt tatggttccg gacacctgca | 5400 |
| agagctaatc cactggcgac acctcaaaga aggtaatcca ctggcgcacg cttggaagcg | 5460 |
| gtataggtat caagcgtgat aatgcaacag ttagaataat tagtttgccc tagccggtat | 5520 |
| tccttggtgt tccaataggg ttccgaagcc aataggcgaa aaagctgact tttcagtccc | 5580 |
| ttttattatt caattcgctt cggtccaagc ataattgtaa cgctacgtga tagaaaaatg | 5640 |
| gaaattgaca gattacttac ttaaattaat ataatctatt aatatcgtca agctaaaaac | 5700 |
| atgtaatacg taaatatatg gaactttat gtctgaaaag accacattat tattgatcgt | 5760 |
| aatacactga actggtcata acagggaagg ctaactgcaa catatcctat aaatactcag | 5820 |
| tgaaaatggc cgctcccaa tgttaagcca ttttgcggt cgggctaagc gctcgtccgt | 5880 |
| gtctcccctg gcccgagtgt cggctctcca tcagcggcct catcatctgt cgctgacacc | 5940 |
| ggtggcccca atttcaaatc gaggaaagac gatgccctcg ccggcaaacg tcgac | 5995 |

<210> SEQ ID NO 3
<211> LENGTH: 303
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3

| | |
|---|---|
| atggaattag ccggactaaa cgtcgccggc atggcccaga ccttcggagt attatcgctc | 60 |
| gtctgttcta agcttgttag gcgtgcaaag gccaagagga aggccaaacg ggtatccccg | 120 |
| ggcgaacgcg accatcttgc tgagccagcc aatctgagca ccactccttt ggccatgact | 180 |
| tcccaagccc gaccgggacg ttcaacgacc cgcgagttgc tgcgaaggga ccctttgtcg | 240 |
| ccggacgtga aaattcagac ctacgggatt aatacgcatt tcgaaacaaa cctacgggat | 300 |
| taa | 303 |

<210> SEQ ID NO 4
<211> LENGTH: 780
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4

| | |
|---|---|
| atggatccca aattgctatt ccttccacga tttcaaccag tagatctcac tccagcatgg | 60 |
| agccagataa accttattcga ggggatccga tttgcttttg caatctatag ccgtgactat | 120 |
| agcaaacccc tcctgcattt ccagaaacga tgggctcttg cagtgctaga tttgaaggaa | 180 |
| aactctccac cgatatatat acttaaacaa ctagctgagc tcttgaagaa caaagtctgc | 240 |
| tatcatcctc ctatgtttgt tagtcagccg gatctggctc gagaaaacga ccaacatgta | 300 |
| tttgtctatc tttctcgcga gaagatgcag aaagtgctga aggaacaatc cattacattt | 360 |
| ggaatggagg ccgtgctggc gacaacgatt caaccatatc ggagcgagct cgccctccag | 420 |
| gagatgctcc gtgttcacaa ccttgcttgg ccgcacagcc gcacgaagga acctgattta | 480 |
| gaatgcttca tcgccatttt cgcaagttcc ttgttcattc acttgctgga gttaaaagtg | 540 |

```
accaacgttt acgggagaga ggtagcttgc accttctttc tgcggcgagg gactgaaaac    600 cgccctatg atgttgtagc ttgcggcacc acacaattca ccaaaaatgc cctcgggata    660
tcacgtccgg ccgcctcctc accggagcca gacctaaccc tgcgactctc ggggcctgat    720
caggaaggcg aggagggcgt catgaagcct gctgcagtaa acctgaagaa agaagcctaa    780
```

<210> SEQ ID NO 5
<211> LENGTH: 543
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5

```
atggctgaag acgacctgtg ttctctcttt ttcaagctca aagtggagga tgtgacaagc     60
agcgatgagc tagctagaca catgaagaac gcctcaaatg agcgtaaacc cttgatcgag    120
ccgggtgaga atcaatcgat ggatattgac gaagaaggag ggtcggtggg ccacgggctg    180
ctgtacctct acgtcgactg cccgacgatg atgctctgct tctatggagg gtccttgcct    240
tacaattgga tgcaaggcgc actcctcacc aaccttcccc cgtaccagca tgatgtgact    300
ctcgatgagg tcaatagagg gctcaggcaa gcatcaggtt ttttcggtta cgcggatcct    360
atgcggagcg cctacttcgc tgcatttttct ttccctgggc gtgtcatcaa gctgaatgag    420
cagatggagc taacttcgac aaagggaaag tgtctgacat cgacctcta tgccagcacc    480 cagcttaggt tcgaacctgg tgagttggtg aggcatggcg agtgcaagtt tgcaatcggc    540
taa                                                                  543
```

<210> SEQ ID NO 6
<211> LENGTH: 603
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6

```
atggctcgtt attgcagtgg tggctctcaa cggcttcatg tcgatgattt tcgttggatc     60
aaggagccca ctcgactgaa ggctcagctt attaatgtgg tggagaccta caaggctgca    120
caaacagaga cgttaaagta ctatatatca tctgcaactg agcgtgtggc tcatgtggag    180
gcagccgagg tcaacaatgc ggaaatggag ctgcatcctg ctgggttgaa gtaccctctg    240
tccttcgtct ttacctcct ggccgtggct acagcctgca aggagaacaa gcatctcttg    300
tgcgaggagc atttggaggg ggacttgata tcgtgcgtcg ttcctcccta tcagacaaat    360
gtctcactcg ctgctttaag ggagctccac aattccattt cgggaggagg gtaccaggaa    420
caagcagaca tggattattt tgtggcgatc atcccaaatg ataatttcga ctatcagagc    480
tgcgaaatcg acacacgaag ttgcggtaaa ggactttgca agatttatag tagggaactg    540
ggagggcagc ctctagctta tgacgccata ctggcaatcg gcaaggtgct gctgctggaa    600
tag                                                                  603
```

<210> SEQ ID NO 7
<211> LENGTH: 2250
<212> TYPE: DNA
<213> ORGANISM: Artificial Sequence
<220> FEATURE:

<223> OTHER INFORMATION: Description of Artificial Sequence: Synthetic polynucleotide

<400> SEQUENCE: 7

```
atggctggat cctccttcac attgccatca actggctcag cgccccttga tatgatgctt      60
atcgatgatt cagatctgct gcaattgggt ctccagcagg tattctcgaa gcggtacaca     120
gagacaccgc agtcacgcta caaactgacc aggagggctt ctccagacgt ctcatctggc     180
gaaggcaatg tgcatgccct tgcgttcata tatgtcaacg ctgagacgtt gcagatgatc     240
aaaaacgctc gatcgctaac cgaagcgaac ggcgtcaaag atcttgtcgc catcgacgtt     300
ccgccatttc gaaacgactt ctcaagagcg ctactccttc aagtgatcaa cttgttggga     360
aacaaccgaa atgccgatga cgatcttagt cacttcatag cagttgctct cccaaacagc     420
gcccgctcta agatcctaac cacggcaccg ttcgaaggaa gcttgtcaga aaacttcagg     480
gggttcccga tcactcgtga aggaaatgtg gcatgtgaag tgctagccta tgggaataac     540
ttgatgccca aggcctgctc cgattccttt ccaaccgtgg atcttcttta tgactatggc     600
aagttcttcg agagttgcgc ggccgatgga cgtatcggtt attttcctga aggcgttacg     660
aaacctaaag tggctataat tggcgcaggc ttttccgggc tcgttgcagc gagcgaacta     720
cttcatgcag gggtagacga tgttacggtg tatgaggcga gtgatcggct tggaggaaag     780
ctatggtcac acggatttaa gagtgctcca aatgtgatag ccgagatggg ggccatgcgt     840
tttccgcgaa gtgaatcatg cttgttcttc tatctcaaaa agcacggact ggactccgtt     900
ggtctgttcc cgaatccggg aagtgtcgat accgcattgt tctacagggg ccgtcaatat     960
atctggaaag cgggagagga gccaccggag ctgtttcgtc gtgtgcacca tggatggcgc    1020
gcattttttgc aagatggcta tctccatgat ggagtcatgt tggcgtcacc gttagcaatt    1080
gttgacgcct tgaatttagg gcatctacag caggcgcatg gcttctggca atcttggctc    1140
acatattttg agcgagagtc tttctcttct ggcatcgaaa aaatgttctt gggcaatcat    1200
cctccggggg gtgaacaatg gaattcccta gatgacttgg atcttttcaa agcgctgggt    1260
attggatccg gcggattcgg ccctgtattt gaaagtgggt ttatcgagat ccttcgctta    1320
gtcgtcaacg ggtatgagga taacgtgcgg ctgagttacg aaggaatttc tgagctgcct    1380
cataggatcg cctcacaggt aattaacggc agatctattc gcgagcgtac aattcacgtt    1440
caagtcgagc agattgatag agaggaggat aaaataaata tcaagatcaa aggaggaaag    1500
gttgaggtct atgatcgagt actggttaca tccgggtttg cgaacatcga aatgcgccat    1560
ctcctgacat caagcaacgc attcttccat gcagatgtaa gccatgcaat agggaacagt    1620
catatgactg gtgcgtcaaa actgttcttg ctgactaacg aaaaattctg gctacaacat    1680
catttgccat cgtgcatact caccaccggc gttgcaaagg cagtttattg cttagactat    1740
gatccgcgag atccaagcgg caaaggactg gtgttgataa gctatacttg ggaggatgac    1800
tcacataagc tcctagccgt ccccgacaaa agagaaaggt tcgcatcgct gcagcgcgat    1860
attgggaggg cattcccaga ttttgccaag cacctaactc ctgcagacgg aactatgat    1920
gataatatcg ttcaacatga ttggctgact gatccccacg ctggcggagc gtttaaactg    1980
aaccgcagag gcaacgacgt atattcagaa aggcttttct ttcagccctt tgacgtaatg    2040
catcccgcgg acgataaggg actttacttg gccggttgta gctgttcctt caccggaggg    2100
tgggttcatg gtgccattca gaccgcatgc aacgctacgt gtgcgatcat ttatggttcc    2160
ggacacctgc aagagctaat ccactggcga cacctcaaag aaggtaatcc actggcgcac    2220
```

```
gcttggaagc ggtataggta tcaagcgtga                                      2250

<210> SEQ ID NO 8
<211> LENGTH: 1401
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8
atggtgaccc tctcctcgat caccgagacg cttaaatgtc tcagggaaag aaaatactcg      60
tgctttgagt taatcgaaac gataatagcc cgctgtgaag cagcaagatc cttaaacgcc     120
tttctggaaa ccgactgggc gcacctacgg tggactgcca gcaaaatcga tcaacacgga     180
ggtgccggtg ttggcctagc tggcgttccc ctatgcttta aagcgaatat tgcgacaggc     240
aggttcgccg cgaccgctgg tacgccaggc ttacagaacc acaaacccaa gacgcctgcc     300
ggagttgcac gacaacttct cgcggctggg gcactgcctg cgcttcggg aaacatgcac      360 gaattgtctt ttgggatcac gagcaacaac ttcgccacag gcgccgtacg aaacccgtgg     420
aaccctagtc tcatcccagg gggatcaagt ggggtgtgg ccgccgcggt ggccggccga      480
ttgatgctgg gcggcgtcgg aactgacacg ggagcgtcgg tccgtttacc ggccgccttg     540
tgcggcgtgg tggggtttcg tcctaccgtg gggcgatatc caacgacgg aatagttccg      600 gtaagcccca cccgggacac ccctggcgtt atcgcacaga atgttccgga cgtgattctt     660
cttgacggta tcatttgcgg gagaccgccg gttaatcaaa cggtccgcct gaaggggctg     720
cgtataggct tgccaaccgc ttacttttac aacgacctgg agcccgatgt cgccttagca     780
gccgagacga ttatcagagt tctggcacgc aaagatgtta cttttgttga agcagatatt     840
cctgatttag cgcatcacaa tgaaggggtc agctttccga ctgccatcta cgaatttccg     900
ttgtcccttg aacattatat tcagaacttc gtagagggtg tttcctttc tgaggttgtc      960 agagcgattc gcagtccgga tgttgcaagt attctcaatg cacaactctc ggataatctt    1020
atttccaaaa gcgagtattg tctggcgcga cgttttttca gaccgagact ccaagcggcc    1080
taccacagtt acttcaaggc gcatcagcta gatgcaattc ttttcccaac agctccgttg    1140
acagccaagc caattggcca tgatctatcg gtgattcaca atggctcaat gaccgatacc    1200
tttaaaatct tcgtgcggaa tgtagatccc agcagtaatg cgggcctgcc gggcctaagt    1260
cttcccgttt ctcttagttc caacggtctg cctattggca tggaaatcga tggctctgca    1320
agctcggatg aacgtctgtt agcaattgga ctagcgatag aagaagcaat agactttagg    1380
catcgtccga ctctgtcgta a                                             1401

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ccaatctgag caccactcct                                                  20

<210> SEQ ID NO 10
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 10
aatcccgtag gtttgtttcg                                                   20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gatatcccga gggcattttt                                                   20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
gaatgcttca tcgccatttt                                                   20

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
caatagaggg ctcaggcaag                                                   20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
cctcaccaac tcaccaggtt                                                   20

<210> SEQ ID NO 15
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
gcgaagtgga tgtctttgg                                                    19

<210> SEQ ID NO 16
<211> LENGTH: 21
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 16
ttgcgaggta cactggactg a                                               21

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
gcaggacgtg atctgactga                                                 20

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
gacggacgag ctactcttgg                                                 20
```

AGROBACTERIUM RHIZOGENES TRANSFORMATION AND EXPRESSION OF ROL GENES IN KALANCHOË

SEQUENCE LISTING

The instant application contains a Sequence Listing which has been submitted in ASCII format via EFS-Web and is hereby incorporated by reference in its entirety. Said ASCII copy, created on May 30, 2013 is named 48374-0122 SL.txt and is 44,954 bytes in size.

FIELD

The present disclosure embraces *Kalanchoë* interspecific hybrid plants, and considers rol transformation in *Kalanchoë* species and hybrids.

INTRODUCTION

*Kalanchoë blossfeldiana*, and its cultivars, is a horticulturally important plant due to its popularity as both an indoor and outdoor plant. The genus of *Kalanchoë* belongs to the sedum family (Crassulaceae), and there are more than 100 different species of *Kalanchoë*, most of which are found in Madagascar and South Africa, and a few in Asia and South America. *Kalanchoë* are succulent plants, characterized by turgid leaves that enable the plants to survive drought conditions. Consequently, *Kalanchoë* are useful ornamental plants because they can survive in less than optimal growing conditions.

*Kalanchoë* displays an elongated growth habit in nature, which is considered undesirable for the potted plant industry that favors more compact plant architecture for space and transportation purposes. Thus, the industry treats *Kalanchoë* plants with chemical growth retardants to alter plant shape and size.

SUMMARY

In one aspect, there is provided a species-independent method for transforming a Kalanchoë interspecific hybrid plant, comprising: (a) co-cultivating wild-type *A. rhizogenes* with a *Kalanchoë* interspecific hybrid plant, wherein *A. rhizogenes* transfers one or more rol genes into said plant; (b) selecting a putatively transformed root having a hairy root phenotype; (c) growing the root on a regeneration medium; (d) regenerating a shoot from the root, thereby generating a plantlet, and; (e) growing the plantlet into a mature plant. In one embodiment, the method further comprises assaying the presence of one or more rol genes in the mature plant.

In another aspect, provided is a method for producing a *Kalanchoë* interspecific hybrid plant having intermediate compactness, comprising: (a) transforming *Kalanchoë* plant tissue with *A. rhizogenes*, wherein *A. rhizogenes* delivers and integrates one or more rol genes into plant genome; (b) selecting a putatively transformed root having a hairy root phenotype; (c) growing the root on a regeneration medium; (d) regenerating a shoot from the root, thereby generating a plantlet; (e) growing said plantlet into a mature plant, and; (f) selecting a plant having intermediate compactness, wherein intermediate compactness is from about 5% to about 50% of a non-transformed control plant.

In another aspect, provided is a method for reducing the height of a *Kalanchoë* interspecific hybrid plant by about 5% to about 60%, compared to a wild-type control plant, comprising: (a) transforming *Kalanchoë* plant tissue with *A. rhizogenes*, wherein *A. rhizogenes* delivers and integrates one or more rol genes into hybrid plant genome; (b) selecting a putatively transformed root having a hairy root phenotype; (c) growing said root on a regeneration medium; (d) regenerating a shoot from said root, thereby generating a plantlet; (e) growing said plantlet into a mature plant, and; (f) selecting a plant having reduced height compared to a non-transformed control plant.

In another aspect, the disclosure provides a rol-transformed *Kalanchoë* interspecific hybrid with intermediate height, wherein said intermediate height is about 5% to about 60% of a control, non-transformed *Kalanchoë* interspecific hybrid plant.

In another aspect, provided herein is a *Kalanchoë* interspecific hybrid comprising one or more rol genes.

DETAILED DESCRIPTION

Figure 1:
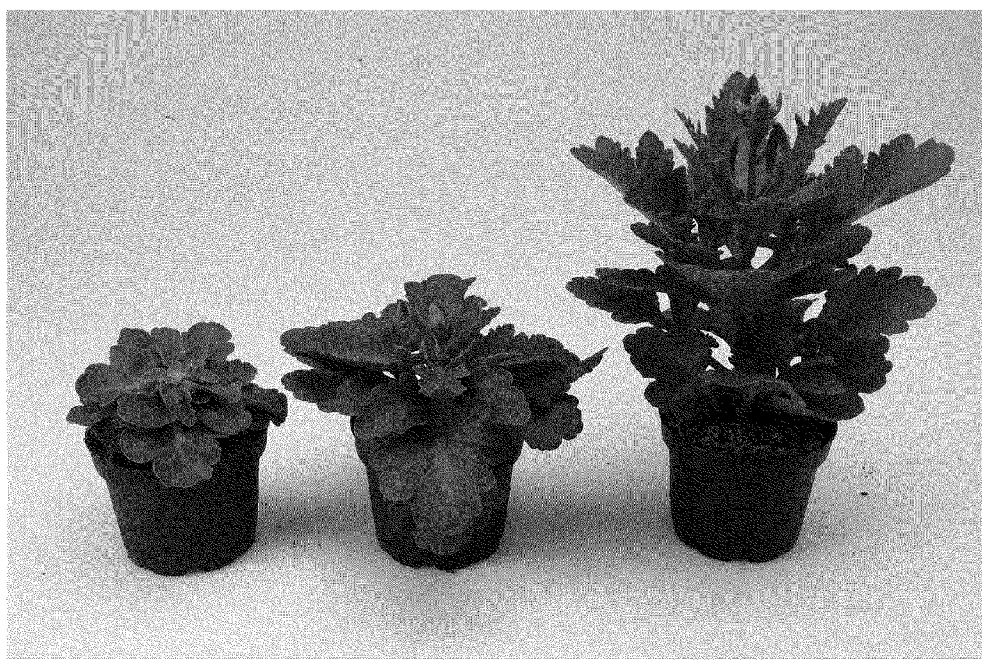
FIG. 1 illustrates double-type *Kalanchoë* interspecific hybrid 2006-0199 plants in early generative stage after 6 weeks under short day conditions. Plants labeled from left to right: on the left is a rol transformed line (line 6a); in the middle is an intermediate line (line 3a), and on the right is an untransformed control plant.
Figure 2:
FIG. 2 illustrates double-type *Kalanchoë* interspecific hybrid 2006-0199 plants in generative stage after 12 weeks under short day conditions. Plants labeled from left to right: on the left is a rol transformed line (line 6a); in left middle position is an intermediate line (line 3a1), in the right middle position is an intermediate line (line 3a2) and on the right is an untransformed control plant.
Figure 3:
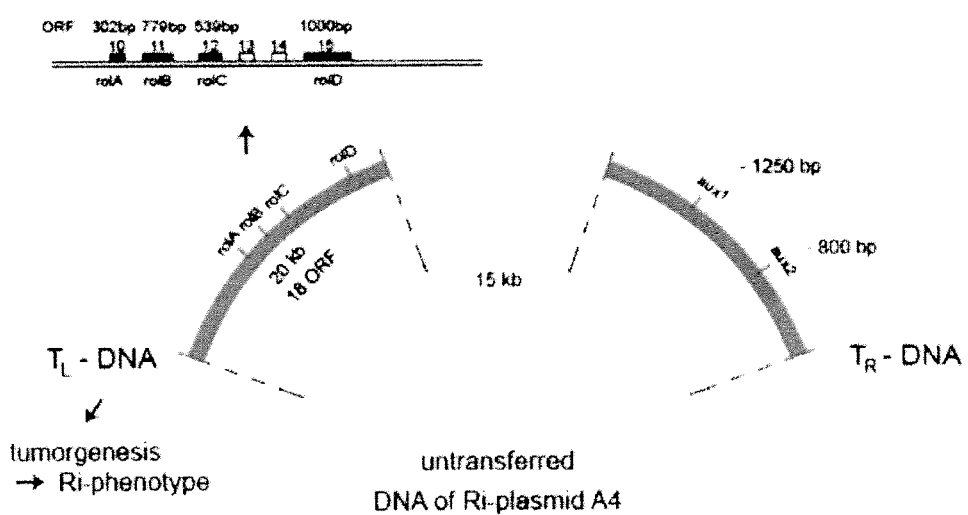
FIG. 3 depicts an illustrative *A. rhizogenes* R1-plasmid from an agropine strain. The T-DNA contains two segments, $T_L$ and $T_R$, which are separated by a 15 Kb sequence that is not integrated. The $T_L$-DNA contains 18 open reading frames (ORFs) where the four root loci-genes reside. The $T_R$-DNA contains several genes, including aux1 and aux2.

The present disclosure embodies methodology and means for transforming *Kalanchoë* species and hybrids with *Agrobacterium rhizogenes* (*A. rhizogenes*), as well as employing *A. rhizogenes* for altering *Kalanchoë* growth and plant architecture.

The Ri-plasmid of naturally occurring soil bacterium *A. rhizogenes* agropine-type strains carry two T-DNA regions ($T_L$-DNA and $T_R$-DNA) on the Ri-plasmid for transfer into plant cells. Following infection of a plant cell, the bacterium transfers the entire T-DNA region (both $T_L$-DNA and $T_R$-DNA), thereby transferring rol (root loci) genes into the plant genome and causing hairy root growth at the site of infection. Tepfer (1984) *Cell,* 37, pp. 959-967. Because *A. rhizogenes* naturally infects plants, the rol genes are naturally transferred into the plant and function as plant oncogenes and develop hairy roots in plant tissues.

The $T_L$-DNA contains four rol genes, rolA, rolB, rolC, and rolD, whereas the $T_R$-DNA contains several genes, including two auxin genes, aux1 and aux2.

Here, the present inventors provide species-independent methodology for transforming a *Kalanchoë* interspecific hybrid with *A. rhizogenes*, as well as methodology for altering *Kalanchoë* interspecific hybrid growth and plant architecture. As described below, the present inventors discovered novel phenotypes, such as intermediate plant height and compactness, that can be obtained through rol introduction.

While any methodology can be used for producing rol-expressing *Kalanchoë* interspecific hybrids, the present disclosure provides both "natural" and "non-natural" methodology for generating rol-transformed *Kalanchoë* interspecific hybrids. For example, and as discussed below, Applicants harnessed wild-type *A. rhizogenes* to transfer its native rol genes into a plant cell. While this is a "natural" system in that *A. rhizogenes* transfers its native rol genes to plant cells, it is extremely unlikely to occur in nature because interspecific hybrids rarely exist, let alone fertile interspecific hybrids. That is, geographical distribution of *Kalanchoë* species does not favor the creation of interspecific hybrids, and in the rare instance of their existence, the interspecific hybrids have low fertility and low seed dispersal. Furthermore, compact plants like rol-transformed *Kalanchoë* face obstacles such as increased risk of fungal infection due to compact leaves forming closed canopy structure, as well as competitiveness from neighboring plants.

All technical terms used herein are terms commonly used in biochemistry, molecular biology and agriculture, and can be understood by one of ordinary skill in the art. Technical terms can be found in: Molecular Cloning: A Laboratory Manual, 3rd ed., vol. 1-3, ed. Sambrook and Russell, Cold Spring Harbor Laboratory Press, Cold Spring Harbor, N.Y., 2001; Current Protocols in Molecular Biology, ed. Ausubel et al., Greene Publishing Associates and Wiley-Interscience, New York, 1988 (with periodic updates); Short Protocols in Molecular Biology: A Compendium of Methods from Current Protocols in Molecular Biology, 5th ed., vol. 1-2, ed. Ausubel et al., John Wiley & Sons, Inc., 2002; Genome Analysis: A Laboratory Manual, vol. 1-2, ed. Green et al., Cold Spring Harbor Laboratory Press, Cold Spring Harbor, N.Y., 1997. Methodology involving plant biology techniques is described herein and is described in detail in treatises such as Methods in Plant Molecular Biology: A Laboratory Course Manual, ed. Maliga et al., Cold Spring Harbor Laboratory Press, Cold Spring Harbor, N.Y., 1995. Various techniques using PCR are described in Innis et al., PCR Protocols: A Guide to Methods and Applications, Academic Press, San Diego, 1990 and in Dieffenbach and Dveksler, PCR Primer: A Laboratory Manual, 2nd ed., Cold Spring Harbor Laboratory Press, Cold Spring Harbor, N.Y., 2003. PCR-primer pairs can be derived from known sequences by known techniques such as using computer programs intended for that purpose, Primer, Version 0.5, 1991, Whitehead Institute for Biomedical Research, Cambridge, Mass. Methods for chemical synthesis of nucleic acids are discussed, for example, in Beaucage and Caruthers, 1981, Tetra. Letts. 22: 1859-1862, and Matteucci and Caruthers, 1981 J. Am. Chem. Soc. 103: 3185. Restriction enzyme digestions, phosphorylations, ligations and transformations were done as described in Sambrook et al., Molecular Cloning: A Laboratory Manual, 2nd ed. (1989), Cold Spring Harbor Laboratory Press. All reagents and materials used for the growth and maintenance of bacterial cells were obtained from Aldrich Chemicals (Milwaukee, Wis.), DIFCO Laboratories (Detroit, Mich.), Invitrogen (Gaithersburg, Md.), or Sigma Chemical Company (St. Louis, Mo.), unless otherwise specified.

"Transformation" refers to any methodology for introducing a rol gene(s) into a host plant cell. Importantly, and because *A. rhizogenes* naturally infects plants, transformation includes the natural transfer of wild-type rol genes from wild-type bacterium into a plant cell. Thus, and as used herein, transformation neither implies nor requires cloning a heterologous gene into a vector for transfer into a host plant cell. Furthermore, a host plant cell expressing a rol gene(s) may be characterized as "transformed." Transformation may occur by any known method including, for example, natural infection, floral dip, infiltration, or particle bombardment. Transformation of a cell may be detected by any known means, including but not limited to Northern Blot, Southern blot, PCR, and/or RT-PCR.

The term "tissue culture" refers to plant tissues propagated under sterile conditions, often for producing clones of a plant. Plant tissue culture relies on the fact that many plant cells have the ability to regenerate a whole plant. Single cells, plant cells without cell walls (protoplasts), pieces of leaves, or roots can often be used to generate a new plant on culture media given the required nutrients and plant hormones.

"*Kalanchoë* interspecific hybrid" embraces any *Kalanchoë* plant with an interspecific cross in its background. That is, interspecific hybrids include both the first and subsequent generations of crosses between two *Kalanchoë* species, as well as the progeny produced from either selfing an interspecific hybrid or crossing an interspecific hybrid with a *Kalanchoë* of the same or different species.

*A. rhizogenes* refers to *Agrobacterium rhizogenes* and its Ri-plasmid from an agropine strain. The T-DNA contains two segments, $T_L$ and $T_R$, which are separated by a 15 Kb sequence that is not integrated. The $T_L$-DNA contains 18 open reading frames (ORFS) where the four root loci-genes reside. The $T_R$-DNA contains several genes, including aux1 and aux2.

"Hairy root phenotype" refers to a plant phenotype indicative of a putative transformed plant. That is, when *A. rhizogenes* infects a plant cell and transfer one or more rol genes, hairy root growth occurs at the infection site. In this way, a hairy root phenotype offers a marker-free method for indentifying putative transformants.

"Intermediate height" refers to a quantitative reduction of plant height relative to a wild-type or control plant of the same species. The height of the transformed plant can be decreased from about 5% to about 60%, preferably from 10% to about 50%, even more preferably from 15% to about 50% of the height of a wild type plant.

"Intermediate compactness" refers to a quantitative reduction of plant compactness relative to a wild-type or control plant of the same species. The compactness of the transformed plant can be increased from about 5% to about 50%, preferably from 10% to about 50%, even more preferably from 15% to about 50% of the height of a wild type plant.

A. Nucleic Acid Sequences

The term "gene" refers to a nucleic acid (e.g., DNA or RNA) sequence that comprises coding sequences necessary for the production of RNA or a polypeptide. A polypeptide can be encoded by a full-length coding sequence or by any part thereof. The term "parts thereof" when used in reference to a gene refers to fragments of that gene, particularly a fragment encoding at least a portion of a protein. The fragments may range in size from a few nucleotides to the entire gene sequence minus one nucleotide. Thus, "a nucleic acid sequence comprising at least a part of a gene" may comprise fragments of the gene or the entire gene.

"Gene" also encompasses the coding regions of a structural gene and includes sequences located adjacent to the coding region on both the 5' and 3' ends for a distance of about 1 kb on either end such that the gene corresponds to the length of the full-length mRNA. The sequences which are located 5' of the coding region and which are present on the mRNA are referred to as 5' non-translated (or untranslated) sequences (5' UTR). The sequences which are located 3' or downstream of the coding region and which are present on the mRNA are referred to as 3' non-translated (or untranslated) sequences (3' UTR).

"Nucleic acid" as used herein refers to RNA or DNA that is linear or branched, single or double stranded, or a hybrid thereof. The term also encompasses RNA/DNA hybrids.

"Encoding" and "coding" refer to the process by which a gene, through the mechanisms of transcription and translation, provides information to a cell from which a series of amino acids can be assembled into a specific amino acid sequence to produce an active enzyme. Because of the degeneracy of the genetic code, certain base changes in DNA sequence do not change the amino acid sequence of a protein. It is therefore understood that modifications in the DNA sequence encoding transcription factors which do not substantially affect the functional properties of the protein are contemplated.

The term "expression," as used herein, refers to the production of a functional end-product e.g., an mRNA or a protein.

The terms "polypeptide," "peptide" and "protein" are used interchangeably herein to refer to a polymer of amino acid residues. The terms apply to amino acid polymers in which one or more amino acid residue is an artificial chemical analog of a corresponding naturally occurring amino acid, as well as to naturally occurring amino acid polymers.

Probe or primer refers to a short oligonucleotide sequence that could be designed and synthesized, or generated as a fragment of a larger sequence. A probe or primer can be any length, such as 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 nucleotides in length.

Illustrative rol sequences include but are not limited to the sequences set forth in SEQ ID NOs: 1-18, respectively, as well as nucleic acid molecules comprised of fragments or variants of SEQ ID NO: 1-18 with one or more bases deleted, substituted, inserted, or added, which variant codes for a polypeptide with rol activity. For example, and in no way limiting, the present disclosure provides SEQ ID NO: 1, as well as various fragments of SEQ ID NO: 1, which could include, for example, rolA-D and aux1-2. For instance, and as readily apparent to one of ordinary skill in the art, the rolA gene could represent a 700 bp portion or fragment of a larger sequence comprising rolA-D and aux1-2.

A "variant" is a nucleotide or amino acid sequence that deviates from the standard, or given, nucleotide or amino acid sequence of a particular gene or protein. The terms "isoform," "isotype," and "analog" also refer to "variant" forms of a nucleotide or an amino acid sequence. An amino acid sequence that is altered by the addition, removal, or substitution of one or more amino acids, or a change in nucleotide sequence, may be considered a "variant" sequence. The variant may have "conservative" changes, wherein a substituted amino acid has similar structural or chemical properties, e.g., replacement of leucine with isoleucine. A variant may have "nonconservative" changes, e.g., replacement of a glycine with a tryptophan. Analogous minor variations may also include amino acid deletions or insertions, or both. Guidance in determining which amino acid residues may be substituted, inserted, or deleted may be found using computer programs well known in the art such as Vector NTI Suite (InforMax, Md.) software. "Variant" may also refer to a "shuffled gene" such as those described in Maxygen-assigned patents.

Included in the category of "variant" sequences are sequences that hybridize to a reference rol sequence. For example, two sequences hybridize when they form a double-stranded complex in a hybridization solution of 6×SSC, 0.5% SDS, 5×Denhardt's solution and 100 μg of non-specific carrier DNA. See Ausubel et al., supra, at section 2.9, supplement 27 (1994). Sequences may hybridize at "moderate stringency," which is defined as a temperature of 60.degree. C. in a hybridization solution of 6.times.SSC, 0.5% SDS, 5.times. Denhardt's solution and 100.mu.g of non-specific carrier DNA. For "high stringency" hybridization, the temperature is increased to 68.degree. C. Following the moderate stringency hybridization reaction, the nucleotides are washed in a solution of 2.times.SSC plus 0.05% SDS for five times at room temperature, with subsequent washes with 0.1.times.SSC plus 0.1% SDS at 60.degree. C. for 1 hour. For high stringency, the wash temperature is increased to 68.degree. C. One with ordinary skill in the art can readily select such conditions by varying the temperature during the hybridization reaction and washing process, the salt concentration during the hybridization reaction and washing process, and so forth. For present purposes, hybridized nucleotides can be detected using 1 ng of a radiolabeled probe having a specific radioactivity of 10,000 cpm/ng, where the hybridized nucleotides are clearly visible following exposure to X-ray film at −70.degree. C. for no more than 72 hours.

The present application is directed to such nucleic acid molecules that are at least 60%, 65%, 70%, 75%, 80%, 85%, 90%, 95%, 96%, 97%, 98%, 99% or 100% identical to a nucleic acid sequence described in any of SEQ ID NO: 1-18. Preferred are nucleic acid molecules which are at least 95%, 96%, 97%, 98%, 99% or 100% identical to the nucleic acid sequence shown in any of SEQ ID NO: 1-18. Differences between two nucleic acid sequences may occur at the 5' or 3' terminal positions of the reference nucleotide As a practical matter, stating whether any particular nucleic acid molecule is at least 95%, 96%, 97%, 98% or 99% identical to a reference nucleotide sequence implicates a comparison made between two molecules, using algorithms known in the art and can be determined conventionally using publicly available computer programs such as the blastn algorithm (National Center for Biotechnology, Bethesda, Md., US). See Altschul et al., Nucleic Acids Res. 25: 3389-402 (1997). The terms "sequence identity" and "sequence similarity" can be determined by alignment of two peptide or two nucleotide sequences using global or local alignment algorithms. Sequences may then be referred to as "substantially identical" or "essentially similar" when they share at least 70% of sequence identity over their entire length, respectively. Sequence alignments and scores for percentage sequence identity may be determined using computer programs, such as the GCG Wisconsin Package, Version 10.3, available from Accelrys Inc., 9685 Scranton Road, San Diego, Calif. 92121-3752 USA, or EmbossWin version 2.10.0 (using the program "needle"). Alternatively percent similarity or identity may be determined by searching against databases, using algorithm as FASTA, BLAST, etc.

The present disclosure may contemplate nucleic acid molecules encoding functional proteins. As known in the art, it is understood that such proteins encompass amino acid substitutions, additions, and deletions that do not alter the function of any of the proteins.

Because many proteins are encoded by gene families, it is expected that other genes could encode proteins with similar functions as the instant polypeptides. These genes can be identified and functionally annotated by sequence comparison. A worker skilled in the art can identify a functionally related protein sequence with the aid of conventional methods such as screening cDNA libraries or genomic libraries with suitable hybridization probes. The skilled artisan knows that paralogous sequences can also be isolated with the aid of (degenerate) oligonucleotides and PCR-based methods.

B. Nucleic Acid Constructs

As explained above, one or more rol sequences are transferred into a host plant cell. Such transfer can occur through natural means, such as natural infection of plant cell with *A. rhizogenes* carrying native rol genes. Such natural or native transfer avoids the need for constructs and selection markers.

However, in another aspect, one or more rol sequences can be incorporated into a nucleic acid construct that is suitable for introduction into a plant cell. Thus, in instance where a native system is not employed, a nucleic acid construct can be used to express rol in a plant cell.

Exemplary nucleic acid constructs may comprise a base sequence of a minimum length to generate a mRNA and consequently a polypeptide. There is no theoretical upper limit to the base sequence length. The preparation of such constructs is described in more detail below.

As a source of the nucleic acid sequence for transcription, a suitable cDNA or genomic DNA or synthetic polynucleotide may be used. Methods for the isolation of suitable rol sequences are described, supra. Sequences coding for the whole, or substantially the whole, of the sequence may thus be obtained. Suitable lengths of this DNA sequence may be cut out for use by means of restriction enzymes. When using genomic DNA as the source of a partial base sequence for transcription, it is possible to use either intron or exon regions or a combination of both.

Recombinant nucleic acid constructs may be made using standard techniques. For example, the nucleic acid sequence for transcription may be obtained by treating a vector containing said sequence with restriction enzymes to cut out the appropriate segment. The nucleic acid sequence for transcription may also be generated by annealing and ligating synthetic oligonucleotides or by using synthetic oligonucleotides in a polymerase chain reaction (PCR) to give suitable restriction sites at each end. The nucleic acid sequence then is cloned into a vector containing suitable regulatory elements, such as upstream promoter and downstream terminator sequences.

Another aspect concerns a nucleic acid construct wherein a rol sequence is operably linked to one or more regulatory sequences, which drive expression of the rol sequence in certain cell types, organs, or tissues without unduly affecting normal development or plant physiology.

Of course, and in the context of a natural transformation or natural infection system, native or endogenous regulatory sequences are used, rather than heterologous sequences.

"Promoter" connotes a region of DNA upstream from the start of transcription that is involved in recognition and binding of RNA polymerase and other proteins to initiate transcription. A "constitutive promoter" is one that is active throughout the life of the plant and under most environmental conditions. Tissue-specific, tissue-preferred, cell type-specific, and inducible promoters constitute the class of "non-constitutive promoters." "Operably linked" refers to a functional linkage between a promoter and a second sequence, where the promoter sequence initiates and mediates transcription of the DNA sequence corresponding to the second sequence. In general, "operably linked" means that the nucleic acid sequences being linked are contiguous.

Promoters useful for expression of a nucleic acid sequence introduced into a cell may include native or endogenous promoters for natural transformation systems, or constitutive promoters, such as the cauliflower mosaic virus (CaMV) 35S promoter, or tissue-specific, tissue-preferred, cell type-specific, and inducible promoters. For example, by using vascular system-specific, xylem-specific, or xylem-preferred promoters, one can modify rol expression specifically in many tissues such as vascular tissues, especially xylem. The use of a constitutive promoter in general affects enzyme levels and functions in all parts of the plant, while use of a tissue-preferred promoter permits targeting of the modified gene expression to specific plant parts, leading to a more controllable phenotypes.

A vector may also contain a termination sequence, positioned downstream of a rol sequence, such that transcription of mRNA is terminated, and polyA sequences added. Exemplary of such terminators are native or endogenous terminator sequenes, cauliflower mosaic virus (CaMV) 35S terminator, or the nopaline synthase gene (Tnos) terminator. The expression vector also may contain enhancers, start codons, splicing signal sequences, and targeting sequences.

Expression vectors may also contain a selection marker by which transformed cells can be identified in culture. The marker may be associated with the heterologous nucleic acid molecule, i.e., the gene operably linked to a promoter. As used herein, the term "marker" refers to a gene encoding a trait or a phenotype that permits the selection of or the screening for, a plant or cell containing the marker. In plants, for example, the marker gene will encode antibiotic or herbicide resistance. This allows for selection of transformed cells from among cells that are not transformed or transfected.

Examples of suitable selectable markers include adenosine deaminase, dihydrofolate reductase, hygromycin-B-phosphotransferase, thymidne kinase, xanthine-guanine phosphoribosyltransferase, glyphosate and glufosinate resistance, and amino-glycoside 3'-O-phosphotranserase (kanamycin, neomycin and G418 resistance). These markers may include resistance to G418, hygromycin, bleomycin, kanamycin, and gentamicin. The construct may also contain the selectable marker gene Bar that confers resistance to herbicidal phosphinothricin analogs like ammonium gluphosinate. Thompson et al., EMBO J. 9: 2519-23 (1987). Other suitable selection markers are known as well.

Visible markers such as green florescent protein (GFP) may be used. Methods for identifying or selecting transformed plants based on the control of cell division have also been described. See WO 2000/52168 and WO 2001/059086. Likewise, the presence of a distinguishing phenotype, such as tumor or hairy root growth, may also be used for identification and selection.

In a natural transformation or natural infection system, a selection marker is not employed. Because infection provides its own distinct and natural phenotype, a transformed cell can be selected based on a post-infection phenotype, such as hairy root phenotype.

Replication sequences, of bacterial or viral origin, may also be included to allow the vector to be cloned in a bacterial or phage host. Preferably, a broad host range prokaryotic origin of replication is used. A selectable marker for bacteria may be included to allow selection of bacterial cells bearing the desired construct. Suitable prokaryotic selectable markers also include resistance to antibiotics such as kanamycin or tetracycline.

Other nucleic acid sequences encoding additional functions may also be present in the vector, as is known in the art. For instance, when *Agrobacterium* is the host, T-DNA sequences may be included to facilitate the subsequent transfer to and incorporation into plant chromosomes.

C. *Kalanchoë* Species and Interspecific Hybrids

As used herein, "interspecific hybrid" includes the progeny from the cross of two different species of *Kalanchoë* and its cultivars, as well as progeny resulting from subsequent backcrossing to one of the parents. This backcrossing to one of the parents may be conducted one or more times with the goal of stably combining the double-type trait with desired characteristics.

*K. blossfeldiana* can be crossed with numerous other *Kalanchoë* species to combine advantageous characteristics into unique new cultivars. Among the numerous interspecific hybrids that may be created are *K. blossfeldiana*×*K. laciniata, K. blossfeldiana*×*K. rotundifolia, K. blossfeldiana*×*K. aromatica, K. blossfeldiana*×*K. pubescens, K. blossfeldiana*×*K. grandiflora, K. blossfeldiana*×*K. citrina, K. blossfeldiana*×*K. ambolensis, K. blossfeldiana*×*K. faustii, K blossfeldiana*×*K. schumacherii, K. blossfeldiana*×*K. pritwitzii, K. blossfeldiana*×*K. flammea, K. blossfeldiana*×*K. figueredoi, K. blossfeldiana*×*K. rauhii, K. blossfeldiana*×*K. obtusa, K. blossfeldiana*×*K. pumila, K. blossfeldiana*×*K. marmorata, K. blossfeldiana*×*K. porphyrocalux, K. blossfeldiana*×*K. jongmansii, K. blossfeldiana*×*K. pinnata, K. blossfeldiana*×*K. daigremontiana, K blossfeldiana*×*K. gracilipes, K blossfeldiana*×*K. campanulata, K blossfeldiana*×*K. latisepela, K. blossfeldiana*×*K. coccinea, K. blossfeldiana*×*K. fedtschenkoi, K. blossfeldiana*×*K. tubiflora, K. blossfeldiana*×*K. decumbens, K. blossfeldiana*×*K. manginii, K. blossfeldiana*×*K. orgyalis, K. blossfeldiana*×*K. crenata* and *K. blossfeldiana*×*K. tomentosa.*

As a first step in making interspecific hybrids, a single or double-type *Kalanchoë* plant selection is crossed with a single-type *Kalanchoë* selection from another species. Progeny are screened for fertile selections. Large numbers of progeny may have to be screened to identify fertile selections. The fertile selections may be screened for those exhibiting the double-type flower trait if one of the parents was a double-type selection. Alternatively, the single-type fertile interspecific hybrid is crossed, either as the male or female parent, with a double-type *Kalanchoë* selection. A double-type hybrid progeny plant with desirable phenotypic characteristics is propagated asexually by conventional methods to determine if the phenotypic characteristics are stable.

For example, a *K. blossfeldiana* (tetraploid)×*K. laciniata* (diploid) interspecific hybrid is by nature triploid and thus sterile. *K. blossfeldiana* times *K. laciniata* interspecific hybrid progeny plants were screened and 'Yellow African', described in U.S. Plant Pat. No. 12,299, was identified. This fertile *K. blossfeldiana*×*K. laciniata* interspecific hybrid has been used to breed a series of interspecific hybrid cultivars designated African Treasures™. One such cultivar was designated 'KJ 2000 0716' and is described in pending U.S. plant patent application Ser. No. 10/654,571.

'KJ 2000 0716' was identified in the progeny originating from a cross between 'Yellow African' and a single-type *K. blossfeldiana*. Three new double-flowered *Kalanchoë* interspecific hybrids originated from crosses between 'KJ 2000 0716' as the female parent, and 'Monroe' as male double-type *K. blossfeldiana* parent. 'Monroe' is described in U.S. Plant Pat. No. 14,714.

Recurrent selection is used to increase the number of petals per flower found in the instant *Kalanchoë* interspecific hybrid plants. A double-type *Kalanchoë* interspecific hybrid plant is selfed, or crossed to another double-type *Kalanchoë* plant, and the progeny screened for plants with double-type flowers with an increased number of petals per flower compared to the double-type parents.

Similar methods as employed for double-type *Kalanchoë* selection are used for recurrent selection to optimize compactness found in the instant rol-transformed *Kalanchoë* interspecific hybrid plants. A rol-transformed *Kalanchoë* interspecific hybrid plant is selfed, or crossed to another *Kalanchoë* plant, and the progeny screened for compactness compared to the rol-transformed parent.

D. Transformation Methodology: Transfer of Rol Genes

As explained above, transformation" refers to any methodology for introducing a rol gene(s) into a host plant or plant cell. Importantly, and because *A. rhizogenes* naturally infects plants, transformation embraces transferring wild-type rol genes from wild-type bacterium into a plant cell. Thus, and as used herein, transformation does not require cloning a heterologous gene into a vector for transfer into a host plant cell, nor does transformation require genetically engineering the bacterium.

"Transformed plant" refers to a plant that comprises a nucleic acid sequence that also is present per se in another organism or species, or that is optimized, relative to host codon usage, from another organism or species. Both monocotyledonous and dicotyledonous angiosperm or gymnosperm plant cells may be transformed in various ways known to the art. For example, see Klein et al., *Biotechnology* 4: 583-590 (1993); Bechtold et al., C. R. Acad. Sci. Paris 316: 1194-1199 (1993); Bent et al., *Mol. Gen. Genet.* 204: 383-396 (1986); Paszowski et al., EMBO J. 3: 2717-2722 (1984); Sagi et al., Plant Cell Rep. 13: 262-266 (1994). *Agrobacterium* species such as *A. tumefaciens* and *A. rhizogenes* can be used, for example, in accordance with Nagel et al., *Microbiol Lett* 67: 325 (1990). Additionally, plants may be transformed by *Rhizobium, Sinorhizobium* or *Mesorhizobium* transformation. Broothaerts et al., *Nature* 433: 629-633 (2005).

For example, *Agrobacterium* may be transformed with a plant expression vector via, e.g., electroporation, after which the *Agrobacterium* is introduced to plant cells via, e.g., the well known leaf-disk method. Additional methods for accomplishing this include, but are not limited to, electroporation, particle gun bombardment, calcium phosphate precipitation, and polyethylene glycol fusion, transfer into germinating pollen grains, direct transformation, Lorz et al., *Mol. Genet.* 199: 179-182 (1985), and other methods known to the art. If a selection marker, such as kanamycin resistance, is employed, it makes it easier to determine which cells have been successfully transformed. Marker genes may be included within pairs of recombination sites recognized by specific recombinases such as cre or flp to facilitate removal of the marker after selection. See U.S. published application No. 2004/0143874.

Transgenic plants without marker genes may be produced using a second plasmid comprising a nucleic acid encoding the marker, distinct from a first plasmid that comprises a rol sequence. The first and second plasmids or portions thereof are introduced into the same plant cell, such that the selectable marker gene that is transiently expressed, transformed plant cells are identified, and transformed plants are obtained in which the rol sequence is stably integrated into the genome and the selectable marker gene is not stably integrated. See U.S. published application No. 2003/0221213.

The *Agrobacterium* transformation methods discussed above are known for transforming dicots. Additionally, de la Pena et al., Nature 325: 274-276 (1987), Rhodes et al., Science 240: 204-207 (1988), and Shimamato et al., Nature 328: 274-276 (1989) have transformed cereal monocots using *Agrobacterium*. Also see Bechtold et al., C.R. Acad. Sci. Paris 316 (1994), illustrating vacuum infiltration for *Agrobacterium*-mediated transformation.

Plant cells may be transformed with a nucleic acid or nucleic acid construct without the use of a selectable or visible marker, and transgenic organisms may be identified by detecting the presence of the introduced sequence or construct. The presence of a protein, polypeptide, or nucleic acid molecule in a particular cell can be measured to determine if, for example, a cell has been successfully transformed or transfected. For example, and as routine in the art, the presence of the introduced construct can be detected by PCR or other suitable methods for detecting a specific nucleic acid or polypeptide sequence. Additionally, transformed cells may be identified by recognizing differences in the growth rate or a morphological feature of a transformed cell compared to the growth rate or a morphological feature of a non-transformed cell that is cultured under similar conditions. See WO 2004/076625.

Methods of regenerating a plant from a transformed cell or culture vary according to the plant species but are based on known methodology. For example, methods for regenerating *Kalanchoë* plants are well-known in the art can be found in Christensen, B., Sriskandarajah, S., Serek, M., Müller, R., 2008. Transformation of *Kalanchoë* blossfeldiana with rol-genes is useful in molecular breeding towards compact growth. *Plant Cell Rep.* 27, 1485-1495.

E. Plant Growth Conditions

The instant *Kalanchoë* plants described herein were grown in a greenhouse at 64.4 degree F. during the day and 68 degree F. during the night. The plants were produced in pots with a diameter of 10.5 cm or 13 cm. Cuttings were grown under long-day conditions (16 hours light, 8 hours night) during the first 3-8 weeks following planting, depending on cultivar and pot size. Between 4-9 weeks after planting, the plants were transferred to short-day conditions (10 hour light and 14 hour dark). The flowering is induced by short-day conditions. Between 13-19 weeks after planting, depending on cultivar, pot size, and time of year, the plants were mature with flowers that were opening or about to open.

The plants were grown under natural light conditions supplemented with 70.μmol photons $m^{-2}$ $s^{-1}$ SON-T light when the natural light was less than 100.mu.mol/m2/s. Plants were grown in a peat based soil mix and were watered with a solution containing 200 parts per million (ppm) nitrogen, 200 ppm potassium, 40 ppm phosphorous, 200 ppm calcium, 40 ppm magnesium, 60 ppm sulphate, 1 ppm iron, 0.6 ppm manganese, 0.1 ppm copper, 0.1 ppm zinc, 0.3 ppm borium, 0.03 ppm molybdenum.

F. Selection and Analysis of Rol-Transformed Plants

The present rol-transformed plants are selected that contain and express one or more rol genes relative to a control, non-transformed plant of the same species. Additionally, the instant plants may have an altered phenotype relative to a non-transformed control plant. Such phenotype may include an intermediate height or intermediate compactness, wherein the transformed plant has a reduced height and/or compactness relative to the control plant.

The phrase "intermediate height" refers to a quantitative reduction of plant height relative to a wild-type or control plant of the same species. The height of the transformed plant can be decreased from about 5% to about 60%, preferably from 10% to about 50%, even more preferably from 15% to about 50% of the height of a wild type plant.

The phrase "intermediate compactness" refers to a quantitative reduction of plant compactness relative to a wild-type or control plant of the same species. The compactness of the transformed plant can be increased from about 5% to about 50%, preferably from 10% to about 40%, even more preferably from 15% to about 50% of the height of a wild type plant.

The following examples are illustrative and do not limit the present application. Of course, it is understood that many variations and modifications can be made while remaining within the intended spirit and scope.

EXAMPLE 1

Transformation Materials and Methodology

Plant Material

In vivo plants of *Kalanchoë grandiflora* and the F1-hybrid 2009-0347 (referred to as 0347) and established in vitro culture plants of *K. blossfeldiana* 'Molly', and *K. grandiflora*, and the F1-hybrid 2006-0199 (referred to as 0199), (Knud Jepsen A/S, Hinnerup, Denmark and KU-LIFE, Crop Sciences, TUstrup). In vivo plants were cultivated in a greenhouse with temperatures of 20° C. at day and night, 16 hour day length and a light intensity of 260 μmol photons $m^{-2}$ $s^{-1}$. In vitro plants were cultivated in growth chamber with temperatures of 25° C. at day and 22° C. at night, 13 hour day length and a light intensity of 75 μmol photons $m^{-2}s^{-1}$. The two F1-hybrids are closely related since 0199 is the paternal part of the crossing to produce 0347.

36, 104, 166, 158 and 128 leaf explants were used for transformation of *K. blossfeldiana* 'Molly', 2006-0199, 2009-0347, *K. grandiflora* and *K. grandiflora*, respectively. 25 leaf explants for each species/hybrid were used for control experiment. Leaves derived from in vivo material were sterilised in 70% EtOH for 1 min. followed by 20 min. in 1% NaOCl (VWR, Copenhagen, Denmark) and 0.03% (v/v) Tween 20 (Merck, La Jolla, USA) and washed 3 times in sterile water and were stored until excision.

Bacterial Strain

*Agrobacterium rhizogenes* strain ATCC43057 (A4) (kindly provided by Dr. David Tepfer, Biologie de la Rhizosphère, INRA, Versailles, France) was used for induction of hairy roots. The strain was cultured in liquid MYA medium (Tepfer and Cassedelbart (1987) *Microbiol Sci.* 4, pp. 24-28. 1 mL of the bacterial glycerol stock (kept at −80° C.) was diluted in 10 mL MYA in a 50 mL Falcon tube and incubated for 8 h at 27° C. and shaken at 260 rpm. The solution was further diluted with 100 mL MYA in a 250 mL flask and shaken at 260 rpm for 24 h in darkness at 27° C. The $OD_{600}$=0.4-0.6 was measured on Nanodrop 1000 (Thermo Scientific, Wilmington, Del., USA).

Transformation

Sterilized leaves or in vitro plant were excised to pieces of min 1 cm×1 cm and stored in sterile water until all explants were ready. The water was discarded from the explants and *A. rhizogenes*-suspension was added to cover all explants for 30 min. After 30 min. the *A. rhizogenes*-suspension was discarded and the slices were transferred, with a thin layer of the *A. rhizogenes* suspension on the surface, to co-cultivation plates for 24 h in darkness without selection. The explants were cultivated in the lab at temperatures at 22° C. in darkness. After co-cultivation the explants were transferred to O-media (selection media) by drying the explants with pieces of ripped sterile filter paper. The leaf surface was as dry as possible on both sides of the excised leaf. The explants stayed dark until roots were developed enough to be transferred to regeneration media. The material was transformed over three sessions. Firstly transformation was conducted with *K. blossfeldiana* 'Molly' and *K. gracilipes*, secondly; 0347 and *K. grandiflora* and finally with 0199. For each species/hybrid the controls and putative transformants was performed the same day.

Basic Medium

The basic medium used as background of all media used was ½×MS (Sigma M0404) (consisting of Murashige and Skoog macro- and microelements) (Murashige and Skoog, 1962) at a concentration of 2.2 g $L^{-1}$, 30 g $L^{-1}$ sucrose (table sugar), 7 g $L^{-1}$ bacto agar and 0.50 g $L^{-1}$ 2-(N-morpholino)- ethanesulphonic acid (MES) (Duchefa). The pH was adjusted to 6.3 by 1 M KOH and the media was autoclaved at 121° C. and 103.5 kPa.

Co-Cultivation Medium

Co-cultivation medium used for co-cultivation between explant and *A. rhizogenes* consisted of basic medium with 30 μg mL$^{-1}$ acetosyringone (Sigma-Aldrich, Steinheim, Germany).

Selection Medium

Selection medium was a hormone-free medium used for root formation of putatively transformed explants and controls. Filter-sterilized antibiotics were added after autoclaving to the selection media to the basic medium. Selection media consist of basic media ½×MS medium with timentin (TIM) in the concentration of 100 mg L$^{-1}$. Preferably, the selection medium contains arginine, preferably 0.5 mM arginine.

Regeneration Media

Regeneration medium containing the hormone N-(2-chloro-4-pyridyl)-N-phenylurea (CPPU) was used for regeneration of nodules on the putatively transformed root clusters. Filter-sterilised hormones and antibiotics were added after autoclaving to the regeneration media. The CPPU-medium contained basic ½×MS medium with 1.5 μg L$^{-1}$ CPPU together with TIM in the concentration 100 mg L$^{-1}$.

Co-Cultivation

In all treatments the explants were co-cultivated for 24 hours. After co-cultivation, the explants were blotted onto sterile filter paper and thoroughly dried with ripped pieces of sterilised filter paper. Controls and putatively transformed explants were transferred to selection medium.

Plant Selection

After 24 hours of co-cultivation the explants were transferred to O-media (selection medium) with 8 explants on each Petri dish, with a number total number of Petri dishes of 5, 13, 21, 20 and 16 for 'Molly', 2006-0199, 2009-0347, *K. grandiflora* and *K. gracilipes*, respectively. The increasing number of roots and decreasing number of explants (due to vitrification—the leaf sections became glass like or because of infections) were monitored for the specific Petri dish in the treatment.

Plant Regeneration

When the roots of putatively transformed explants had developed to a length of 1.5-2 cm they were transferred in clusters, with a part of the explant to CPPU-medium. The transferred root clusters were placed in a climate chamber (Celltherm, United Kingdom) on shelves with 11 h daylight and day/night temperatures of 20/18° C. and an intensity of 45-70 mmol photons M$^{-2}$s$^{-1}$ (Philips, Amsterdam, The Netherlands). Only root clusters with *A. rhizogenes* treated explants was transferred. Here the number of root clusters was monitored as well as the number of nodules developing from the roots. Counting of nodule development was stopped when no positive development was observed after 30 days for any of the five species/hybrids. Nodules from *K. gracilipes* were observed losing colour and vigour. An attempt to stop this negative development was made by the addition of 0.1 μg/ml Auxin (NAA). Result is still unknown.

Control Plants

Control plants were treated like transformants but inoculated in MYA medium without bacteria and with a lower number of explants-25 per cultivar. The control experiment plants were conducted in parallel with the transformants.

Molecular Analysis

DNA was isolated with DNeasy Plant Mini Kit (Qiagen, Hilden, Germany) from root clusters (and nodules) on regeneration medium. Half of a root cluster was harvested for DNA extraction from each of the five species/hybrids. The concentration was measured on NanoDrop 1000 (Thermo Scientific, Wilmington, Del., USA). Concentrations was measured to 5.10 ng/μl, 2.34 ng/μl, 4.34 ng/μl, 0.52 ng/μl and 2.06 ng/μl for 0199, 0347, *K. grandiflora, K. gracilipes* and *K. blossfeldiana* 'Molly', respectively. Since the concentration for *K. gracilipes* was too low this was not used for the PCR. PCR on DNA was preformed with a concentration of 15 ng with the three specific primers (see Table 1 below) to amplify the rolB gene on the T$_L$-DNA and KdActin and VirD2 as controls. Dimethyl sulfoxide (DMSO) was added to the PCR reaction to obtain a better unfolding of the DNA. The following temperature program was applied for amplification in the DNA thermal cycler (Mycycler, Biorad, Hercules, Calif., USA): 95° C. for 10 min. (initial denaturation) followed by 40 cycles 95° C. for 30 sec. (denaturation), 58° C. for 30 sec. (annealing) and 72° C. for 15 sec. (elongation), with a final 7 min. elongation at 72° C. The amplified fragments sequences were mixed with orange G (Sigma-Aldrich, SteinHeim, Germany) (40% sucrose (w/v) and 1.5% Orange G (w/v) and Gelred (Biotium, Hayward, Calif., USA) and fractionated in 1% TAE agarose gel.

TABLE 1

Primer Sequences
(Lütken et al., Euphytica
DOI 10.1007/s10681-012-0701-5.)

| Gene | Primer sequence | Product size (bp) |
| --- | --- | --- |
| rolA | 5'-CCAATCTGAGCACCACTCCT-3' (SEQ ID NO: 9) 5'-AATCCCGTAGGTTTGTTTCG-3' (SEQ ID NO: 10) | 153 |
| rolB | 5'-GATATCCCGAGGGCATTTTT-3' (SEQ ID NO: 11) 5'-GAATGCTTCATCGCCATTTT-3' (SEQ ID NO: 12) | 182 |
| rolC | 5'-CAATAGAGGGCTCAGGCAAG-3' (SEQ ID NO: 13) 5'-CCTCACCAACTCACCAGGTT-3' (SEQ ID NO: 14) | 202 |
| rolD | 5'-GCGAAGTGGATGTCTTTGG-3' (SEQ ID NO: 15) 5'-TTGCGAGGTACACTGGACTGA-3' (SEQ ID NO: 16) | 225 |
| KdActin* | 5'-GCAGGACGTGATCTGACTGA-3' (SEQ ID NO: 17) 5'-GACGGACGAGCTACTCTTGG-3' (SEQ ID NO: 18) | 168 |

Statistical Analysis

*K. blossfeldiana* 'Molly', 0199, 0347, *K. grandiflora* and *K. grandiflora*, had a total number of petri dishes of 5, 13, 21, 20 and 16, and a total number of explants of 36, 104, 166, 158, respectively, *K. blossfeldiana* 'Molly' functioned as a reference of the transformation. Similarly, control explants had five replicates but 5 explants per species/hybrids with a total of 25 per species/hybrids. Since the explants may be taken out of the experiment because of infection, the number of explants changed over time. The total number of explants was therefore monitored to obtain a better ratio between number of explants and formation of roots. The number of roots was monitored as the number increased. The average of surviving explants per petri dish and the average of roots per petri dish were calculated. The two averages were used to calculate a ratio for each petri dish to describe the number of roots per explants.

$V_{max}$ (root development/days) was modelled with a linear regression and using the slope. The calculations were performed in Excel. Standard deviations (SD) and students t-test (t-test) were calculated for each observation to verify variation within the individual species/hybrids. SD and t-test was calculated in Excel. ANOVA test was performed with R.

Results

The experiments involved a natural transformation with *Agrobacterium rhizogenes* to study the transformation efficiency for different species and hybrids and for plain material from in vivo and in vitro. Two species; *K. gracilipes* and *K. grandiflora* and two hybrids; 2006-0199 and 2009-0347 was transformed with the conditions that was found optimal for *K. blossfeldiana* 'Molly' by Christensen et al., (2008). *K. blossfeldiana* 'Molly' was used as a control within the transformants since the cultivar formed background of the transformation system.

Root induction and growth were monitored as a total number of roots per petri dish in each treatment. Since some explants were removed due to infection the total number of explants over time was also monitored. This was done to obtain a more unbiased assessment when calculating the number of roots per explant in each plant line.

Root Development on 0-Media

Roots from *K. blossfeldiana* 'Molly' and *K. gracilipes* had a later time to first transfer to regeneration medium (88 and 77 days, respectively) compared to 0199, 0347 and *K. grandiflora* (45, 38 and 38 days, respectively). At the time of the first time of transfer to regeneration medium putative transformants from 0199, *K. grandiflora*, *K. gracilipes* and *K. blossfeldiana* 'Molly' were significantly different from control. Only 0347 was not significantly different at the time of first transfer of root clusters, though data show that this changed after 45 days on selection medium (data not shown).

*K. gracilipes* developed roots fastest (16 days from transfer from co-cultivation medium to selection medium) followed by *K. grandiflora* and 0199 (both 17 days after transfer) and *K. blossfeldiana* 'Molly' (18 days after transfer) and finally 0347 (24 days after transfer).

At the first day of transfer to regeneration medium, *K. blossfeldiana* 'Molly' had the highest number of roots per explant (19.4 roots per explant in average), hereafter 0199 (8.5 roots per explant in average) and *K. grandiflora* (3.1 roots per explant in average) and finally 0347 and *K. gracilipes* (both 2.4 roots per explant in average).

What is claimed is:

1. A species-independent method for transforming a Kalanchoë interspecific hybrid plant, comprising:
   (a) co-cultivating wild-type *A. rhizogenes* with a Kalanchoë interspecific hybrid plant, wherein *A. rhizogenes* transfers one or more rol genes into said plant, wherein said one or more rol genes are selected from the group consisting of rolA, rolB, rolC, and rolD, wherein said one or more rol genes at least includes rolB, wherein the nucleic acid sequence for rolA, rolB, rolC, and rolD has 100% sequence identity with SEQ ID NOs: 3, 4, 5, and 6, respectively;
   (b) selecting a putatively transformed root having a hairy root phenotype;
   (c) growing said root on a regeneration medium;
   (d) regenerating a shoot from said root, thereby generating a plantlet, and;
   (e) growing said plantlet into a mature plant.

2. The method of claim 1, further comprising assaying the presence of one or more rol genes in said mature plant.

3. A method for reducing the height of a *Kalanchoë* interspecific hybrid plant by about 5% to about 60%, compared to a wild-type control plant, comprising:
   (a) transforming *Kalanchoë* plant tissue with *A. rhizogenes*, wherein *A. rhizogenes* delivers and integrates one or more rol genes into hybrid plant genome, wherein said one or more rol genes are selected from the group consisting of rolA, rolB, rolC, and rolD, wherein said one or more rol genes at least includes rolB, wherein the nucleic acid sequence for rolA, rolB, rolC, and rolD has 100% sequence identity with SEQ ID NOs: 3, 4, 5, and 6, respectively;
   (b) selecting a putatively transformed root having a hairy root phenotype;
   (c) growing said root on a regeneration medium;
   (d) regenerating a shoot from said root, thereby generating a plantlet; and
   (e) growing said plantlet into a mature plant, and;
   (f) selecting a plant having a reduced height by about 5% to about 60% compared to the height of a non-transformed control plant of the same species.

4. A rol-transformed *Kalanchoë* interspecific hybrid with intermediate height, wherein said intermediate height is a reduction of height by about 5% to about 60% of the height of a control, non-transformed *Kalanchoë* interspecific hybrid plant, wherein the rot-transformed *Kalanchoë* interspecific hybrid has been transformed with one or more rol genes are selected from the group consisting of rolA, rolB, rolC, and rolD, wherein said one or more rol genes at least includes rolB, wherein the nucleic acid sequence for rolA, rolB, rolC, and rolD has 100% sequence identity with SEQ ID NOs: 3, 4, 5, and 6, respectively.

5. Progeny of a rol transformed *Kalanchoë* interspecific hybrid of claim 4.

* * * * *